United States Patent [19]

Ohtsuka et al.

[11] Patent Number: 5,519,139

[45] Date of Patent: May 21, 1996

[54] AMINOPYRIMIDINE DERIVATIVES AND THEIR PRODUCTION AND USE

[75] Inventors: Toshikazu Ohtsuka, Koka; Moriyasu Masui, Yokkaichi; Takami Takeda, Youkaichi; Michio Masuko; Katsuaki Ohba, both of Koka, all of Japan

[73] Assignee: Shionogi & Co., Ltd., Osaka, Japan

[21] Appl. No.: 448,193

[22] Filed: May 23, 1995

Related U.S. Application Data

[62] Division of Ser. No. 168,217, Dec. 17, 1993, Pat. No. 5,439,911.

[30] Foreign Application Priority Data

Dec. 28, 1992 [JP] Japan ..................................... 4-348535
Feb. 1, 1993 [JP] Japan ..................................... 5-014980

[51] Int. Cl.⁶ ..................... C07D 239/30; C07D 239/34; C07D 401/04
[52] U.S. Cl. .......... 544/295; 544/296; 544/314; 544/318; 544/319; 544/334; 544/333; 544/317; 544/310; 544/329; 544/313; 544/327; 544/328
[58] Field of Search ..................... 544/314, 318, 544/319, 334, 317, 329, 295, 296, 328

[56] References Cited

U.S. PATENT DOCUMENTS

| | | | |
|---|---|---|---|
| 3,860,596 | 1/1975 | Kim et al. | 260/256.4 N |
| 4,435,402 | 3/1984 | Tsuji et al. | 424/251 |
| 4,895,849 | 1/1990 | Yoshioka et al. | 514/241 |
| 4,985,426 | 1/1991 | Yoshioka et al. | 514/241 |

FOREIGN PATENT DOCUMENTS

| | | |
|---|---|---|
| 0481448 | 4/1992 | European Pat. Off. . |
| 2064096 | 7/1972 | Germany . |
| 3205638 | 8/1983 | Germany . |
| 3338859 | 5/1985 | Germany . |
| 2262096 | 6/1993 | United Kingdom . |
| WO93/22291 | 11/1993 | WIPO . |

OTHER PUBLICATIONS

Veale et al., *Journal of Organic Chemistry*, vol. 58, 1993, pp. 4490–4493, "Efficient Method for the Synthesis of 1,4-Disubstituted 5-Carbomethoxypyrimidin-6-Ones".

Machon, *Chemical Abstracts*, vol. 71, 1969, Columbus, Ohio, Abstract No. 13046k, "Isothiazole Derivatives".

Dean et al., *J. Heterocyclic Chemistry*, vol. 19, No. 1, 1982, pp. 171–176, "N-Ethoxycarbonylamidines as Starting Materials and Intermediates in the Synthesis of Heterocyclic Compounds".

*Primary Examiner*—John M. Ford
*Attorney, Agent, or Firm*—Wenderoth, Lind & Ponack

[57] ABSTRACT

There is disclosed a novel 4-aminopyrimidine derivative containing an optionally esterified carboxyl group at the 5-position which has potent fungicidal activity as well as insecticidal and miticidal activity. The compound is useful as agricultural fungicides, insecticides and miticides. There are also disclosed a process for producing the above compound and agricultural fungicidal, insecticidal and miticidal compositions

3 Claims, No Drawings

AMINOPYRIMIDINE DERIVATIVES AND THEIR PRODUCTION AND USE

This is a divisional application of Ser. No. 08/168,217 filed Dec. 17, 1993, now U.S. Pat. No. 5,439,911.

FIELD OF THE INVENTION

The present invention relates to novel aminopyrimidine derivatives useful as agricultural fungicides, insecticides and miticides, and also relates to their production and use.

BACKGROUND OF THE INVENTION

Certain kinds of aminopyrimidine derivatives, especially 4-aminopyrimidine derivatives, are known to have insecticidal activity, miticidal activity and fungicidal activity (JP-A 57-176967, JP-A 63-225364 and JP-A 64-68362).

However, these known aminopyrimidine derivatives do not have satisfactory efficacy, particularly with regard to fungicidal activity. There is still a need for compounds having more potent fungicidal activity.

OBJECTS OF THE INVENTION

The main object of the present invention is to provide novel aminopyrimidine derivatives having potent fungicidal activity as well as insecticidal and miticidal activity.

Another object of the present invention is to provide a process for producing aminopyrimidine derivatives.

Yet another object of the present invention is to provide novel intermediate compounds for the production of the aminopyrimidine derivatives.

Still another object of the present invention is to provide agricultural fungicides, insecticides and miticides containing the above aminopyrimidine derivative.

These objects as well as other objects and advantages of the present invention will become apparent to those skilled in the art from the following description.

SUMMARY OF THE INVENTION

The present inventors have intensively studied to obtain compounds having potent fungicidal activity. As a result, it has been found that novel 4-aminopyrimidine derivatives containing an optionally esterified carboxyl group at the 5-position have potent fungicidal activity as well as insecticidal and miticidal activity. Thus, the present invention has been completed.

According to the present invention, there is provided:

(1) A compound of the formula (I):

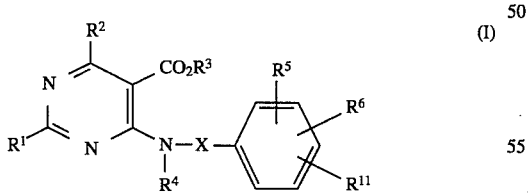

wherein $R^1$ is a hydrogen atom, halogen atom, alkyl, alkylthio, optionally substituted phenyl or optionally substituted heterocyclic group; $R^2$ is alkyl; $R^3$ is a hydrogen atom, alkyl, alkenyl, alkynyl or aralkyl; $R^4$ is a hydrogen atom or alkyl; $R^5$, $R^6$ and $R^{11}$ each is a hydrogen atom, halogen atom, alkoxy, optionally substituted alkyl, alkenyl, alkynyl, optionally substituted hydroxyl, mono- or dialkylamino, alkylthio, alkylsulfinyl, alkylsulfonyl or nitro; and X is alkylene or alkyleneoxy; or a salt thereof;

(2) A process for producing a compound of the formula (I):

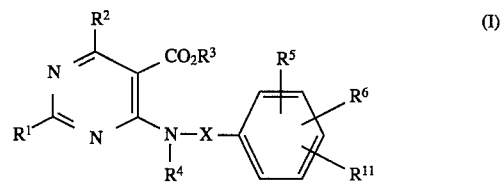

wherein each symbol is as defined above, which comprises reacting a compound of the formula (II):

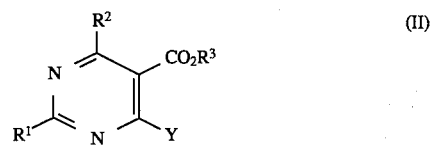

wherein Y is a halogen atom and the other symbols are as defined for the formula (1), with a compound of the formula (III):

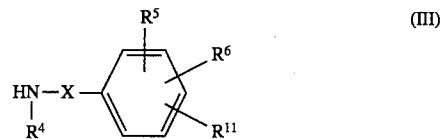

wherein each symbol is as defined above;

(3) An agricultural fungicidal composition comprising a compound of the formula (i) or a salt thereof as an active ingredient;

(4) An insecticidal composition comprising a compound of the formula (I) or a salt thereof as an active ingredient;

(5) A miticidal composition comprising a compound of the formula (I) or a salt thereof as an active ingredient;

6) A process for producing a compound of the formula (I-A):

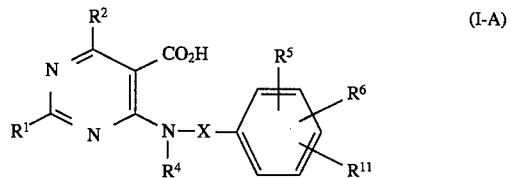

wherein each symbol is as defined for the formula (I), which comprises hydrolyzing a compound of the formula (I-B):

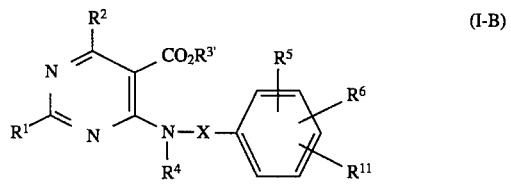

wherein $R^{3'}$ is alkyl, alkenyl, alkynyl or aralkyl, and the other symbols are as defined for the formula (I);

(7) A process for producing a compound of the formula (I-B):

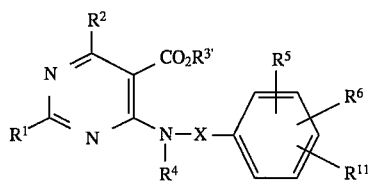
(I-B)

wherein $R^{3'}$ is alkyl, alkenyl, alkynyl or aralkyl, and the other symbols are as defined for the formula (I) which comprises esterifying a compound of the formula (I-A):

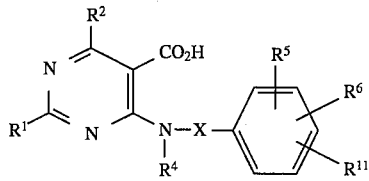
(I-A)

wherein each symbol is as defined above;

(8) A compound of the formula (II):

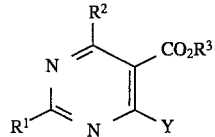
(II)

wherein Y is a halogen atom and the other symbols are as defined for the formula (I), provided that $R^1$ is other than a halogen atom or optionally substituted phenyl; and (9) A compound of the formula (IV):

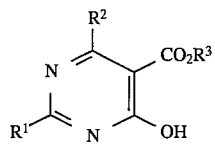
(IV)

wherein each symbol is as defined for the formula (I).

BACKGROUND OF THE INVENTION

Examples of the alkyl represented by $R^1$, $R^2$, $R^3$, $R^4$, $R^5$, $R^6$ and $R^{11}$ include alkyl having 1 to 6 carbon atoms, preferably 1 to 4 carbon atoms, for example, methyl, ethyl propyl, butyl, tert-butyl and the like. Among them, in particular, methyl is preferred for $R^1$, methyl and ethyl are preferred for $R^2$, methyl and ethyl are preferred for $R^3$.

Examples of the alkyl of the alkylthio represented by $R^1$ include the same groups as described for the alkyl represented by $R^1$.

Examples of the heterocyclic group of the optionally substituted heterocyclic group represented by $R^1$ are 5 to 6 membered heterocyclic groups containing in the ring at least one heteroatom selected from oxygen, sulfur and nitrogen, and it may be a condensed ring with a carbocyclic ring or other heterocyclic ring. Examples of the heterocyclic group include pyridyl, pyrimidinyl, pyrazinyl, thiazolyl, benzothiazolyl, benzofuranyl, benzothienyl, oxazolyl, benzoxazolyl isoxazolyl, pyrazolyl, imidazolyl, quinolyl and the like.

Examples of the substituent of the optionally substituted phenyl represented by $R^1$ and the substituent of the optionally substituted heterocyclic group represented by $R^1$ include a halogen atom (e.g., fluorine, chlorine, bromine, iodine), $C_{1-4}$ alkyl (e.g., methyl, ethyl, propyl, etc.), halo-$C_{1-4}$ alkyl (e.g., trifluoromethyl, 2-chloroethyl, etc.), $C_{1-4}$ alkoxy (e.g., methoxy, ethoxy, propoxy, etc.) and the like.

Examples of the alkenyl represented by $R^3$, $R^5$, $R^6$ and $R^{11}$ include alkenyl having 2 to 6 carbon atoms, preferably 2 to 4 carbon atoms, more preferably 3 to 4 carbon atoms, for example, vinyl, allyl, crotyl and the like.

Examples of the alkynyl represented by $R^3$, $R^5$, $R^6$ and $R^{11}$ include alkynyl having 2 to 6 carbon atoms, preferably 2 to 4 carbon atoms, more preferably 3 to 4 carbon atoms, for example, ethynyl, propargyl, 3-butynyl and the like.

Examples of the aralkyl represented by $R^3$ include $C_{6-10}$ aryl-$C_{1-4}$ alkyl, for example, benzyl, phenethyl and the like.

Examples of the halogen atom represented by $R^1$, $R^5$, $R^6$ and $R^{11}$ include a fluorine atom, chlorine atom, bromine atom and iodine atom.

Examples of the alkoxy represented by $R^5$, $R^6$ and $R^{11}$ include alkoxy having 1 to 6 carbon atoms, preferably 1 to 4 carbon atoms, for example, methoxy, ethoxy, propoxy, butoxy and the like.

Examples of the alkyl of the optionally substituted alkyl represented by $R^5$, $R^6$ and $R^{11}$ include the same groups as those described for the above alkyl represented by $R^1$. Examples of the substituted alkyl include halo-$C_{1-4}$ alkyl (e.g., trifluoromethyl, 2-chloroethyl, etc.), $C_{1-4}$ alkoxy-$C_{1-4}$ alkyl (e.g., methoxymethyl, ethoxyethyl, etc.), hydroxy-$C_{1-4}$ alkyl (e.g., hydroxymethyl, hydroxyethyl, etc.), $C_{1-4}$ alkylsulfonyloxy-$C_{1-4}$ alkyl (e.g., ethylsulfonyloxymethyl, methylsulfonyloxyethyl, etc.), tetrahydropyranyloxy-$C_{1-4}$ alkyl (e.g., tetrahydropyran-2-yloxymethyl, tetrahydropyran-2-yloxyethyl, etc.), mono- or di-$C_{1-4}$ alkylamino-$C_{1-4}$ alkyl (e.g., methylaminoethyl, ethylaminoethyl, dimethylaminoethyl, diethylaminoethyl, etc.), $C_{1-4}$ alkylthio-$C_{1-4}$ alkyl (e.g., methylthioethyl, ethylthioethyl, etc.), $C_{1-4}$ alkylsulfinyl-$C_{1-4}$ alkyl (e.g., ethylsulfinylmethyl, methylsulfinylethyl, etc.), $C_{1-4}$ alkylsulfonyl-$C_{1-4}$ alkyl (e.g., ethylsulfonylmethyl, methylsulfonylethyl, etc.) and the like.

Examples of the substituted hydroxyl represented by $R^5$, $R^6$ and $R^{11}$ include $C_{1-6}$ alkoxy (e.g., methoxy, ethoxy, propoxy, isopropoxy, butoxy, etc.), $C_{2-6}$ alkenyloxy (e.g., vinyloxy, allyloxy, etc.), $C_{2-6}$ alkynyloxy (e.g., ethynyloxy, propargyloxy, etc.), halo-$C_{1-6}$ alkoxy (e.g., difluoromethyloxy, 2-chloroethyloxy, etc.), $C_{1-4}$ alkoxy-$C_{1-4}$ alkoxy (e.g., ethoxymethoxy, ethoxyethoxy, etc.), hydroxy-$C_{1-4}$ alkoxy (e.g., hydroxymethoxy, hydroxyethoxy, etc.), $C_{1-4}$ alkylthio-$C_{1-4}$ alkoxy (e.g., ethylthiomethoxy, methylthioethoxy, etc.), $C_{1-4}$ alkylsulfonyloxy-$C_{1-4}$ alkoxy (e.g., methylsulfonyloxyethoxy, ethylsulfonyloxymethoxy, etc.), $C_{1-4}$ alkylsulfinyl-$C_{1-4}$ alkoxy (e.g., methylsulfinylethoxy, ethylsulfinylmethoxy, etc.), $C_{1-4}$ alkylsulfonyl-$C_{1-4}$ alkoxy (e.g., methylsulfonylethoxy, ethylsulfonylmethoxy, etc.), mono- or di-$C_{1-4}$ alkylamino-$C_{1-4}$ alkoxy (e.g., dimethylaminoethoxy, ethylaminoethoxy, etc.), tetrahydropyranyloxy-$C_{1-4}$ alkoxy (e.g., tetrahydropyran-2-yloxymethoxy, tetrahydropyran-2-yloxyethoxy, etc.), optionally substituted phenoxy (e.g., phenoxy, 4-fluorophenoxy, etc.) and the like.

Examples of the mono- or dialkylamino represented by $R^5$, $R^6$ and $R^{11}$ include mono- or dialkylamino having the same alkyl as that represented by $R^1$, for example, butylamino, diethylamino and the like.

Examples of the alkylthio represented by $R^5$, $R^6$ and $R^{11}$ include alkylthio having the same alkyl as that represented by $R^1$, for example methylthio, ethylthio, propylthio, butylthio and the like.

Examples of the alkylsulfinyl represented by $R^5$, $R^6$ and $R^{11}$ include alkylsulfinyl having the same alkyl as represented by $R^1$, for example, methylsulfinyl, ethylsulfinyl, propylsulfinyl and the like.

Examples of the alkylsulfonyl represented by $R^5$, $R^6$ and $R^{11}$ include alkylsulfonyl having the same alkyl as represented by $R^1$, for example, methylsulfonyl, ethylsulfonyl, propylsulfonyl and the like.

$R^5$, $R^6$ and $R^{11}$ may be at any possible position in the benzene ring. The benzene ring preferably has one substituent other than a hydrogen atom preferably at the 4-position.

Examples of the alkylene represented by X include straight-chain or branched-chain alkylene having 1 to 6 carbon atoms, for example, methylene, ethylene, —CH(CH$_3$)—, —CH(C$_2$H$_5$)— and the like.

Examples of the alkyleneoxy represented by X include alkyleneoxy having straight-chain or branched-chain alkylene having 1 to 6 carbon atoms, for example, —CH$_2$O—, —CH$_2$CH$_2$O— and the like. The oxygen atom of the alkyleneoxy is attached to the neighboring benzene ring.

When the aminopyrimidine compound of the formula (I) has an asymmetric carbon atom, each optical isomer and racemic mixtures are also included in the scope of the present invention.

When the compound (I) forms acid addition salts, these salts are also included in the scope of the present invention. Examples of the acid forming the acid addition salt include inorganic acids such as hydrochloric acid, hydrobromic acid, nitric acid, sulfuric acid, phosphoric acid; carboxylic acids such as formic acid, oxalic acid, trichloroacetic acid; sulfonic acids such as methanesulfonic acid, benzenesulfonic acid and the like.

The aminopyrimidine compound of the formula (I) of the present invention is preferably that wherein $R^5$ is a hydrogen atom, halogen atom, alkyl or alkoxy; $R^6$ is a halogen atom, optionally substituted alkyl, alkenyl, alkynyl, optionally substituted hydroxyl, mono- or dialkylamino, alkylthio, alkylsulfinyl, alkylsulfonyl or nitro; and $R^{11}$ is a hydrogen atom.

The aminopyrimidine compound of the formula (I) of the present invention is more preferably that wherein $R^5$ is a hydrogen atom, halogen atom, alkyl or alkoxy; $R^6$ is a halogen atom, alkyl, alkenyl, alkynyl, haloalkyl, alkoxyalkyl, hydroxyalkyl, alkylsulfonyloxyalkyl, tetrahydropyranyloxyalkyl, mono- or dialkylaminoalkyl, alkylthioalkyl, alkylsulfinylalkyl, alkylsulfonylalkyl, alkoxy, alkenyloxy, alkynyloxy, haloalkoxy, alkoxyalkoxy, hydroxyalkoxy, alkylsulfonyloxyalkoxy, alkylthioalkoxy, alkylsulfinylalkoxy, alkylsulfonyl alkoxy, mono- or dialkylaminoalkoxy, tetrahydropyranyloxyalkoxy, optionally substituted phenoxy, mono- or dialkylamino, alkylthio, alkylsulfinyl, alkylsulfonyl or nitro; and $R^{11}$ is a hydrogen atom.

Among them, more preferred aminopyrimidine compound of the formula (I) is that wherein $R^1$ is a hydrogen atom or methyl; $R^2$ is methyl or ethyl; $R^3$ is $C_{1-4}$ alkyl, $C_{3-4}$ alkenyl or $C_{3-4}$ alkynyl; $R^4$ is a hydrogen atom; $R^5$ is a hydrogen atom, halogen atom or alkyl ; $R^6$ is alkyl, alkoxy, haloalkoxy or alkoxyalkyl; $R^{11}$ is a hydrogen atom; and X is —CH$_2$CH$_2$—.

Examples of the pyrimidine derivatives (Compound Nos. 1 to 327) of the formula (I) of the present invention are shown in the following Tables 1 to 34 but are not to be construed to limit the scope of the invention.

TABLE 1

| No | $R^1$ | $R^2$ | $R^3$ | $R^4$ | X | Ar |
|---|---|---|---|---|---|---|
| 1 | H | $C_2H_5$ | $C_2H_5$ | H | —CH$_2$CH$_2$— | 4-C(CH$_3$)$_3$-phenyl |
| 2 | H | $C_2H_5$ | CH$_3$ | H | —CH$_2$CH$_2$— | 4-OC$_4$H$_9$-phenyl |
| 3 | H | $C_2H_5$ | $C_2H_5$ | H | —CH$_2$CH$_2$— | 4-OC$_4$H$_9$-phenyl |
| 4 | H | $C_2H_5$ | $C_2H_5$ | CH$_3$ | —CH$_2$CH$_2$— | 4-OC$_4$H$_9$-phenyl |
| 5 | H | $C_2H_5$ | $C_2H_5$ | H | —CH(CH$_3$)— | 4-OC$_4$H$_9$-phenyl |

TABLE 1-continued

Structure: pyrimidine with R¹, R², CO₂R³, N(R⁴)-X-phenyl(R⁵, R⁶)

| No | R¹ | R² | R³ | R⁴ | X | Aryl (R⁵, R⁶, R¹¹) |
|----|----|----|----|----|---|---------------------|
| 6 | H | C₂H₅ | C₂H₅ | H | —CH(C₂H₅)— | 4-OC₄H₉-phenyl |
| 7 | H | C₂H₅ | C₂H₅ | H | —CH₂— | 4-OC₄H₉-phenyl |
| 8 | H | CH₃ | C₂H₅ | H | —CH₂CH₂— | 4-OC₄H₉-phenyl |

TABLE 2

| No | R¹ | R² | R³ | R⁴ | X | Aryl (R⁵, R⁶, R¹¹) |
|----|----|----|----|----|---|---------------------|
| 9 | phenyl | C₂H₅ | C₂H₅ | H | —CH₂CH₂— | 4-C(CH₃)₃-phenyl |
| 10 | CH₃ | C₂H₅ | C₂H₅ | H | —CH₂CH₂— | 4-OC₄H₉-phenyl |
| 11 | H | C₂H₅ | CH₃ | H | —CH₂CH₂— | 4-C(CH₃)₃-phenyl |
| 12 | H | C₂H₅ | C₃H₇ | H | —CH₂CH₂— | 4-OC₄H₉-phenyl |
| 13 | H | C₂H₅ | CH(CH₃)₂ | H | —CH₂CH₂— | 4-OC₄H₉-phenyl |
| 14 | H | C₂H₅ | C₄H₉ | H | —CH₂CH₂— | 4-OC₄H₉-phenyl |

TABLE 2-continued

| No | $R^1$ | $R^2$ | $R^3$ | $R^4$ | X | Ar (with $R^5$, $R^6$, $R^{11}$) |
|----|-------|-------|-------|-------|---|-----|
| 15 | H | $C_2H_5$ | $CH_2$–(phenyl) | H | $-CH_2CH_2-$ | –(C$_6$H$_4$)–$OC_4H_9$ |
| 16 | H | $C_2H_5$ | $C_4H_9$ | H | $-CH_2CH_2-$ | –(C$_6$H$_4$)–$C(CH_3)_3$ |
| 17 | H | $C_2H_5$ | $C_2H_5$ | H | $-CH_2CH_2-$ | –(C$_6$H$_4$)–$OC_2H_5$ |

TABLE 3

| No | $R^1$ | $R^2$ | $R^3$ | $R^4$ | X | Ar (with $R^5$, $R^6$, $R^{11}$) |
|----|-------|-------|-------|-------|---|-----|
| 18 | H | $C_2H_5$ | $C_2H_5$ | H | $-CH_2CH_2-$ | –(C$_6$H$_4$)–$OC_3H_7$ |
| 19 | H | $C_2H_5$ | $C_2H_5$ | H | $-CH_2CH_2-$ | –(C$_6$H$_4$)–$OC_6H_{13}$ |
| 20 | H | $C_2H_5$ | $C_2H_5$ | H | $-CH_2CH_2-$ | –(C$_6$H$_4$)–$CH_2CH_2OC_2H_5$ |
| 21 | H | $C_2H_5$ | $C_3H_7$ | H | $-CH_2CH_2-$ | –(C$_6$H$_4$)–$CH_2CH_2OC_2H_5$ |
| 22 | H | $C_2H_5$ | $CH(CH_3)_2$ | H | $-CH_2CH_2-$ | –(C$_6$H$_4$)–$CH_2CH_2OC_2H_5$ |
| 23 | H | $C_2H_5$ | $C_2H_5$ | H | $-CH_2CH_2-$ | –(C$_6$H$_3$)($CH_3$)–Cl |
| 24 | H | $C_2H_5$ | $C_2H_5$ | H | $-CH_2CH_2-$ | –(C$_6$H$_3$)($CH_3$)–$OC_4H_9$ |

TABLE 3-continued

| No | R¹ | R² | R³ | R⁴ | X | Ar(R⁵,R⁶,R¹¹) |
|----|----|----|----|----|---|---------------|
| 25 | H | $C_2H_5$ | $C_2H_5$ | H | $-CH_2CH_2-$ | 2-Cl, 3-$OC_4H_9$-phenyl |
| 26 | H | $C_2H_5$ | $C_2H_5$ | H | $-CH_2CH_2-$ | 2,3-di-$CH_3$-phenyl |

TABLE 4

| No | R¹ | R² | R³ | R⁴ | X | Ar(R⁵,R⁶,R¹¹) |
|----|----|----|----|----|---|---------------|
| 27 | H | $C_2H_5$ | $C_2H_5$ | H | $-CH_2CH_2-$ | 2,5-di-$CH_3$-phenyl |
| 28 | H | $C_2H_5$ | $C_2H_5$ | H | $-CH_2CH_2-$ | 3,4-di-Cl-phenyl |
| 29 | H | $C_2H_5$ | $C_2H_5$ | H | $-CH_2CH_2-$ | 2,4-di-Cl-phenyl |
| 30 | H | $C_2H_5$ | $C_2H_5$ | H | $-CH_2CH_2-$ | 2,6-di-Cl-phenyl |
| 31 | H | $C_2H_5$ | $C_2H_5$ | H | $-CH_2CH_2-$ | 3-$CF_3$-phenyl |
| 32 | H | $C_2H_5$ | $C_2H_5$ | H | $-CH_2CH_2-$ | 2-$OC_4H_9$-phenyl |

TABLE 4-continued

| No | R¹ | R² | R³ | R⁴ | X | Aryl (with $R^5$, $R^6$, $R^{11}$) |
|---|---|---|---|---|---|---|
| 33 | H | $C_2H_5$ | $C_2H_5$ | H | $-CH_2CH_2-$ | phenyl-$OC_4H_9$ (meta) |
| 34 | H | $C_2H_5$ | $C_2H_5$ | H | $-CH_2CH_2O-$ | phenyl-$C(CH_3)_3$ (para) |
| 35 | H | $C_2H_5$ | $C_2H_5$ | H | $-CH_2CH_2O-$ | phenyl-$OC_4H_9$ (para) |

TABLE 5

| No | R¹ | R² | R³ | R⁴ | X | Aryl (with $R^5$, $R^6$, $R^{11}$) |
|---|---|---|---|---|---|---|
| 36 | H | $C_2H_5$ | $C_2H_5$ | H | $-CH_2CH_2-$ | phenyl-$NHC_4H_9$ |
| 37 | H | $C_2H_5$ | $C_2H_5$ | H | $-CH_2CH_2-$ | phenyl-$SC_4H_9$ |
| 38 | H | $C_2H_5$ | $C_2H_5$ | H | $-CH_2CH_2-$ | phenyl-$NO_2$ |
| 39 | H | $C_2H_5$ | $C_2H_5$ | H | $-CH_2CH_2-$ | phenyl-$F$ |
| 40 | H | $C_2H_5$ | $C_2H_5$ | H | $-CH_2CH_2-$ | phenyl-$OCH_2CH_2SCH_3$ |
| 41 | H | $C_2H_5$ | $C_2H_5$ | H | $-CH_2CH_2-$ | phenyl-$OCH_2CH_2S(=O)CH_3$ |
| 42 | H | $C_2H_5$ | $C_2H_5$ | H | $-CH_2CH_2-$ | phenyl-$OCH_2CH_2OC_2H_5$ |

TABLE 5-continued

| No | R¹ | R² | R³ | R⁴ | X | Ar (R⁵, R⁶, R¹¹) |
|----|----|----|----|----|----|------------------|
| 43 | H | C₂H₅ | C₂H₅ | H | —CH₂CH₂— | —C₆H₄—OCH₂CH₂NHC₂H₅ |
| 44 | H | C₂H₅ | C₂H₅ | H | —CH₂CH₂— | —C₆H₄—OCH₂CH₂N(C₂H₅)₂ |

TABLE 6

| No | R¹ | R² | R³ | R⁴ | X | Ar (R⁵, R⁶, R¹¹) |
|----|----|----|----|----|----|------------------|
| 45 | H | C₂H₅ | C₂H₅ | H | —CH₂CH₂— | —C₆H₄—Cl |
| 46 | H | C₂H₅ | C₂H₅ | H | —CH₂CH₂— | —C₆H₄—CH₃ |
| 47 | H | C₂H₅ | C₂H₅ | H | —CH₂CH₂— | —C₆H₄—C₄H₉ |
| 48 | H | C₂H₅ | C₂H₅ | H | —CH₂CH₂— | —C₆H₄—N(C₂H₅)₂ |
| 49 | H | C₂H₅ | C₂H₅ | H | —CH₂CH₂— | —C₆H₄—CH₂CH₂OH |
| 50 | H | C₂H₅ | C₂H₅ | H | —CH₂CH₂— | —C₆H₄—CH₂CH₂OSO₂CH₃ |
| 51 | H | C₂H₅ | C₂H₅ | H | —CH₂CH₂— | —C₆H₄—CH₂CH₂O—(tetrahydropyran-2-yl) |
| 52 | H | C₂H₅ | C₂H₅ | H | —CH₂CH₂— | —C₆H₄—OCH₂CH₂O—(tetrahydropyran-2-yl) |

TABLE 6-continued

| No | R¹ | R² | R³ | R⁴ | X | ![aryl with R⁵, R⁶, R¹¹] |
|----|----|----|----|----|---|---|
| 53 | H | $C_2H_5$ | $C_2H_5$ | H | $-\overset{\displaystyle C_2H_5}{\underset{\displaystyle |}{CH}}-$ | 4-$CH_2CH_2OC_2H_5$-phenyl |

TABLE 7

| No | R¹ | R² | R³ | R⁴ | X | aryl (R⁵, R⁶, R¹¹) |
|----|----|----|----|----|---|---|
| 54 | H | $C_2H_5$ | $C_2H_5$ | H | $-CH_2CH_2-$ | 4-$CH_2CH_2NHCH_3$-phenyl |
| 55 | H | $C_2H_5$ | $C_2H_5$ | H | $-CH_2CH_2-$ | 4-$CH_2CH_2NHC_2H_5$-phenyl |
| 56 | H | $C_2H_5$ | $C_2H_5$ | H | $-CH_2CH_2-$ | 4-$CH_2CH_2N(CH_3)_2$-phenyl |
| 57 | H | $C_2H_5$ | $C_2H_5$ | H | $-CH_2CH_2-$ | 4-$CH_2CH_2N(C_2H_5)_2$-phenyl |
| 58 | H | $C_2H_5$ | $C_4H_9$ | H | $-CH_2CH_2-$ | 4-$CH_2CH_2OC_2H_5$-phenyl |
| 59 | H | $C_2H_5$ | $CH_2$-phenyl | H | $-CH_2CH_2-$ | 4-$CH_2CH_2OC_2H_5$-phenyl |
| 60 | H | $C_2H_5$ | $C_2H_5$ | H | $-CH_2CH_2-$ | 4-$CH_2CH_2SC_2H_5$-phenyl |
| 61 | H | $C_2H_5$ | $C_2H_5$ | H | $-CH_2CH_2-$ | 4-$OCH(CH_3)_2$-phenyl |
| 62 | H | $C_2H_5$ | $C_2H_5$ | H | $-CH_2CH_2-$ | 4-$OCH_2CH(CH_3)_2$-phenyl |

TABLE 8

| No | R¹ | R² | R³ | R⁴ | X | Aryl group (R⁵, R⁶, R¹¹) |
|----|----|----|----|----|---|--------------------------|
| 63 | H | $C_2H_5$ | $C_2H_5$ | H | $-CH_2CH_2-$ | 4-($OCH(CH_3)C_2H_5$)-phenyl |
| 64 | H | $C_2H_5$ | $C_2H_5$ | H | $-CH_2CH_2-$ | 4-($OCH_2CH_2CH(CH_3)_2$)-phenyl |
| 65 | H | $C_2H_5$ | $C_2H_5$ | H | $-CH_2CH_2-$ | 4-($OCH(CH_3)C_3H_7$)-phenyl |
| 66 | H | $C_2H_5$ | $C_2H_5$ | H | $-CH(C_2H_5)-$ | 4-(4-fluorophenoxy)phenyl |
| 67 | $SCH_3$ | $C_2H_5$ | $C_2H_5$ | H | $-CH_2CH_2-$ | 3,4-di($OCH_3$)-phenyl |
| 68 | H | $C_2H_5$ | $C_2H_5$ | H | $-CH_2CH_2-$ | 3,4-di($OCH_3$)-phenyl |
| 69 | phenyl | $C_2H_5$ | $C_2H_5$ | H | $-CH_2CH_2-$ | 3,4-di($OCH_3$)-phenyl |
| 70 | H | $C_2H_5$ | $C_2H_5$ | H | $-CH_2CH_2-$ | 4-($OCH_2CH_2OH$)-phenyl |
| 71 | H | $C_2H_5$ | $C_2H_5$ | H | $-CH_2CH_2-$ | 4-($OCH_2CH_2OSO_2CH_3$)-phenyl |

TABLE 9

| No | R¹ | R² | R³ | R⁴ | X | Aryl group (R⁵, R⁶, R¹¹) |
|----|----|----|----|----|---|--------------------------|
| 72 | H | $C_2H_5$ | $C_2H_5$ | H | $-CH_2CH_2-$ | 4-($CH_2CH_2SCH_3$)-phenyl |

TABLE 9-continued

Structure: Aryl group with substituents R⁵, R⁶, R¹¹

| No | R¹ | R² | R³ | R⁴ | X | Aryl |
|---|---|---|---|---|---|---|
| 73 | H | $C_2H_5$ | $C_2H_5$ | H | $-CH_2CH_2-$ | 4-($CH_2CH_2S(O)CH_3$)-phenyl |
| 74 | H | $C_2H_5$ | H | H | $-CH_2CH_2-$ | 4-$OC_4H_9$-phenyl |
| 75 | H | $C_2H_5$ | H | H | $-CH_2CH_2-$ | 4-$C(CH_3)_3$-phenyl |
| 76 | H | $C_2H_5$ | $C_2H_5$ | H | $-CH_2CH_2-$ | 4-$OCHF_2$-phenyl |
| 77 | H | $C_2H_5$ | $C_2H_5$ | H | $-CH_2CH_2-$ | 2,3-di$CH_3$-phenyl |

TABLE 10

| No | R¹ | R² | R³ | R⁴ | X | Aryl |
|---|---|---|---|---|---|---|
| 78 | H | $CH_3$ | $CH_3$ | H | $-CH_2CH_2-$ | 4-$OCH_3$-phenyl |
| 79 | H | $C_2H_5$ | $CH_3$ | H | $-CH_2CH_2-$ | 4-$OCH_3$-phenyl |
| 80 | H | $CH_3$ | $C_2H_5$ | H | $-CH_2CH_2-$ | 4-$OCH_3$-phenyl |
| 81 | H | $C_2H_5$ | $C_2H_5$ | H | $-CH_2CH_2-$ | 4-$OCH_3$-phenyl |
| 82 | $CH_3$ | $CH_3$ | $CH_3$ | H | $-CH_2CH_2-$ | 4-$OCH_3$-phenyl |
| 83 | $CH_3$ | $C_2H_5$ | $CH_3$ | H | $-CH_2CH_2-$ | 4-$OCH_3$-phenyl |
| 84 | $CH_3$ | $CH_3$ | $C_2H_5$ | H | $-CH_2CH_2-$ | 4-$OCH_3$-phenyl |
| 85 | $CH_3$ | $C_2H_5$ | $C_2H_5$ | H | $-CH_2CH_2-$ | 4-$OCH_3$-phenyl |
| 86 | H | $CH_3$ | $CH_3$ | H | $-CH_2CH_2-$ | 4-$OC_2H_5$-phenyl |
| 87 | H | $CH_3$ | $C_2H_5$ | H | $-CH_2CH_2-$ | 4-$OC_2H_5$-phenyl |

TABLE 11

| No | $R^1$ | $R^2$ | $R^3$ | $R^4$ | X | Aryl ($R^5$, $R^6$, $R^{11}$) |
|----|-------|-------|-------|-------|---|----|
| 88 | H | $C_2H_5$ | $CH_3$ | H | $-CH_2CH_2-$ | 4-$OC_2H_5$-phenyl |
| 89 | $CH_3$ | $CH_3$ | $CH_3$ | H | $-CH_2CH_2-$ | 4-$OC_2H_5$-phenyl |
| 90 | $CH_3$ | $C_2H_5$ | $CH_3$ | H | $-CH_2CH_2-$ | 4-$OC_2H_5$-phenyl |
| 91 | $CH_3$ | $CH_3$ | $C_2H_5$ | H | $-CH_2CH_2-$ | 4-$OC_2H_5$-phenyl |
| 92 | $CH_3$ | $C_2H_5$ | $C_2H_5$ | H | $-CH_2CH_2-$ | 4-$OC_2H_5$-phenyl |

TABLE 11-continued

| No | $R^1$ | $R^2$ | $R^3$ | $R^4$ | X | Aryl ($R^5$, $R^6$, $R^{11}$) |
|----|-------|-------|-------|-------|---|----|
| 93 | H | $CH_3$ | $C_2H_5$ | H | $-CH_2CH_2-$ | 4-$OC_3H_7$-phenyl |
| 94 | H | $CH_3$ | $CH_3$ | H | $-CH_2CH_2-$ | 4-$OC_3H_7$-phenyl |
| 95 | H | $C_2H_5$ | $CH_3$ | H | $-CH_2CH_2-$ | 4-$OC_3H_7$-phenyl |
| 96 | $CH_3$ | $CH_3$ | $CH_3$ | H | $-CH_2CH_2-$ | 4-$OC_3H_7$-phenyl |
| 97 | $CH_3$ | $C_2H_5$ | $CH_3$ | H | $-CH_2CH_2-$ | 4-$OC_3H_7$-phenyl |

TABLE 12

| No | $R^1$ | $R^2$ | $R^3$ | $R^4$ | X | Aryl ($R^5$, $R^6$, $R^{11}$) |
|----|-------|-------|-------|-------|---|----|
| 98 | $CH_3$ | $CH_3$ | $C_2H_5$ | H | $-CH_2CH_2-$ | 4-$OC_3H_7$-phenyl |
| 99 | $CH_3$ | $C_2H_5$ | $C_2H_5$ | H | $-CH_2CH_2-$ | 4-$OC_3H_7$-phenyl |
| 100 | H | $CH_3$ | $C_2H_5$ | H | $-CH_2CH_2-$ | 4-$OCH(CH_3)_2$-phenyl |
| 101 | H | $CH_3$ | $CH_3$ | H | $-CH_2CH_2-$ | 4-$OCH(CH_3)_2$-phenyl |
| 102 | H | $C_2H_5$ | $CH_3$ | H | $-CH_2CH_2-$ | 4-$OCH(CH_3)_2$-phenyl |
| 103 | $CH_3$ | $C_2H_5$ | $CH_3$ | H | $-CH_2CH_2-$ | 4-$OCH(CH_3)_2$-phenyl |

TABLE 12-continued

| No | R¹ | R² | R³ | R⁴ | X | Ar (R⁵, R⁶, R¹¹) |
|---|---|---|---|---|---|---|
| 104 | CH₃ | C₂H₅ | C₂H₅ | H | —CH₂CH₂— | 4-OCH(CH₃)₂-C₆H₄— |
| 105 | CH₃ | CH₃ | C₂H₅ | H | —CH₂CH₂— | 4-OCH(CH₃)₂-C₆H₄— |
| 106 | CH₃ | CH₃ | CH₃ | H | —CH₂CH₂— | 4-OCH(CH₃)₂-C₆H₄— |
| 107 | H | CH₃ | CH₃ | H | —CH₂CH₂— | 4-OC₄H₉-C₆H₄— |

TABLE 13

| No | R¹ | R² | R³ | R⁴ | X | Ar (R⁵, R⁶, R¹¹) |
|---|---|---|---|---|---|---|
| 108 | CH₃ | CH₃ | CH₃ | H | —CH₂CH₂— | 4-OC₄H₉-C₆H₄— |
| 109 | CH₃ | CH₃ | C₂H₅ | H | —CH₂CH₂— | 4-OC₄H₉-C₆H₄— |
| 110 | CH₃ | C₂H₅ | CH₃ | H | —CH₂CH₂— | 4-OC₄H₉-C₆H₄— |
| 111 | H | C₂H₅ | CH₃ | H | —CH₂CH₂— | 4-OCH₂CH(CH₃)₂-C₆H₄— |
| 112 | H | CH₃ | CH₃ | H | —CH₂CH₂— | 4-OCH₂CH(CH₃)₂-C₆H₄— |
| 113 | H | CH₃ | C₂H₅ | H | —CH₂CH₂— | 4-OCH₂CH(CH₃)₂-C₆H₄— |
| 114 | CH₃ | CH₃ | C₂H₅ | H | —CH₂CH₂— | 4-OCH₂CH(CH₃)₂-C₆H₄— |

TABLE 13-continued

| No | R¹ | R² | R³ | R⁴ | X | Aryl group |
|---|---|---|---|---|---|---|
| 115 | CH₃ | CH₃ | CH₃ | H | —CH₂CH₂— | 4-OCH₂CH(CH₃)₂-C₆H₄— |
| 116 | CH₃ | C₂H₅ | C₂H₅ | H | —CH₂CH₂— | 4-OCH₂CH(CH₃)₂-C₆H₄— |
| 117 | CH₂ | C₂H₅ | CH₃ | H | —CH₂CH₂— | 4-OCH₂CH(CH₃)₂-C₆H₄— |

TABLE 14

| No | R¹ | R² | R³ | R⁴ | X | Aryl group |
|---|---|---|---|---|---|---|
| 118 | H | C₂H₅ | CH₃ | H | —CH₂CH₂— | 4-OCHF₂-C₆H₄— |
| 119 | H | CH₃ | CH₃ | H | —CH₂CH₂— | 4-OCHF₂-C₆H₄— |
| 120 | H | CH₃ | C₂H₅ | H | —CH₂CH₂— | 4-OCHF₂-C₆H₄— |
| 121 | CH₃ | CH₃ | C₂H₅ | H | —CH₂CH₂— | 4-OCHF₂-C₆H₄— |
| 122 | CH₃ | CH₃ | CH₃ | H | —CH₂CH₂— | 4-OCHF₂-C₆H₄— |
| 123 | CH₃ | C₂H₅ | CH₃ | H | —CH₂CH₂— | 4-OCHF₂-C₆H₄— |
| 124 | CH₃ | C₂H₅ | C₂H₅ | H | —CH₂CH₂— | 4-OCHF₂-C₆H₄— |
| 125 | H | CH₃ | C₂H₅ | H | —CH₂CH₂— | 4-C₄H₉-C₆H₄— |

TABLE 14-continued

| No | R¹ | R² | R³ | R⁴ | X | Aryl (R⁵, R⁶, R¹¹) |
|---|---|---|---|---|---|---|
| 126 | H | CH₃ | CH₃ | H | —CH₂CH₂— | 4-C₄H₉-phenyl |
| 127 | H | C₂H₅ | CH₃ | H | —CH₂CH₂— | 4-C₄H₉-phenyl |

TABLE 15

| No | R¹ | R² | R³ | R⁴ | X | Aryl (R⁵, R⁶, R¹¹) |
|---|---|---|---|---|---|---|
| 128 | CH₃ | C₂H₅ | CH₃ | H | —CH₂CH₂— | 4-C₄H₉-phenyl |
| 129 | CH₃ | C₂H₅ | C₂H₅ | H | —CH₂CH₂— | 4-C₄H₉-phenyl |
| 130 | CH₃ | CH₃ | C₂H₅ | H | —CH₂CH₂— | 4-C₄H₉-phenyl |
| 131 | CH₃ | CH₃ | CH₃ | H | —CH₂CH₂— | 4-C₄H₉-phenyl |
| 132 | H | CH₃ | CH₃ | H | —CH₂CH₂— | 4-C₂H₅-phenyl |
| 133 | H | CH₃ | C₂H₅ | H | —CH₂CH₂— | 4-C₂H₅-phenyl |
| 134 | H | C₂H₅ | C₂H₅ | H | —CH₂CH₂— | 4-C₂H₅-phenyl |
| 135 | H | C₂H₅ | CH₃ | H | —CH₂CH₂— | 4-C₂H₅-phenyl |
| 136 | CH₃ | C₂H₅ | CH₃ | H | —CH₂CH₂— | 4-C₂H₅-phenyl |

TABLE 15-continued

| No | R¹ | R² | R³ | R⁴ | X | Ar (R⁵, R⁶, R¹¹) |
|---|---|---|---|---|---|---|
| 137 | CH₃ | C₂H₅ | C₂H₅ | H | —CH₂CH₂— | —C₆H₄—C₂H₅ |

TABLE 16

| No | R¹ | R² | R³ | R⁴ | X | Ar (R⁵, R⁶, R¹¹) |
|---|---|---|---|---|---|---|
| 138 | CH₃ | CH₃ | C₂H₅ | H | —CH₂CH₂— | —C₆H₄—C₂H₅ |
| 139 | CH₃ | CH₃ | CH₃ | H | —CH₂CH₂— | —C₆H₄—C₂H₅ |
| 140 | H | CH₃ | CH₃ | H | —CH₂CH₂— | —C₆H₄—C₃H₇ |
| 141 | H | CH₃ | C₂H₅ | H | —CH₂CH₂— | —C₆H₄—C₃H₇ |
| 142 | H | C₂H₅ | CH₃ | H | —CH₂CH₂— | —C₆H₄—C₃H₇ |
| 143 | H | C₂H₅ | C₂H₅ | H | —CH₂CH₂— | —C₆H₄—C₃H₇ |
| 144 | CH₃ | C₂H₅ | C₂H₅ | H | —CH₂CH₂— | —C₆H₄—C₃H₇ |
| 145 | CH₃ | C₂H₅ | CH₃ | H | —CH₂CH₂— | —C₆H₄—C₃H₇ |
| 146 | CH₃ | CH₃ | CH₃ | H | —CH₂CH₂— | —C₆H₄—C₃H₇ |

TABLE 16-continued
| No | R¹ | R² | R³ | R⁴ | X | (aryl with R⁵, R⁶, R¹¹) |
|---|---|---|---|---|---|---|
| 147 | CH₃ | CH₃ | C₂H₅ | H | —CH₂CH₂— | 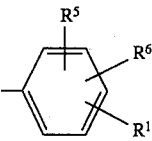 —C₃H₇ |
TABLE 17
| No | R¹ | R² | R³ | R⁴ | X | (aryl with R⁵, R⁶, R¹¹) |
|---|---|---|---|---|---|---|
| 148 | H | CH₃ | C₂H₅ | H | —CH₂CH₂— | 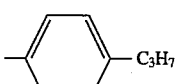 —C(CH₃)₃ |
| 149 | H | CH₃ | CH₃ | H | —CH₂CH₂— | 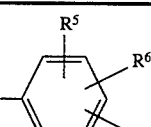 —C(CH₃)₃ |
| 150 | CH₃ | CH₃ | CH₃ | H | —CH₂CH₂— | 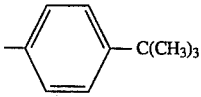 —C(CH₃)₃ |
| 151 | CH₃ | CH₃ | C₂H₅ | H | —CH₂CH₂— | 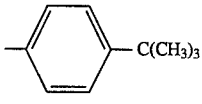 —C(CH₃)₃ |
| 152 | CH₃ | C₂H₅ | C₂H₅ | H | —CH₂CH₂— | 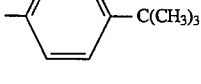 —C(CH₃)₃ |
| 153 | CH₃ | C₂H₅ | CH₃ | H | —CH₂CH₂— | 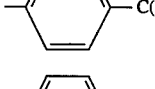 —C(CH₃)₃ |
| 154 | H | C₂H₅ | CH₃ | H | —CH₂CH₂— |  CH₃, —OC₄H₉ |
| 155 | H | CH₃ | CH₃ | H | —CH₂CH₂— | 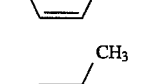 CH₃, —OC₄H₉ |
| 156 | H | CH₃ | C₂H₅ | H | —CH₂CH₂— | 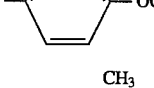 CH₃, —OC₄H₉ |

TABLE 17-continued

| No | R¹ | R² | R³ | R⁴ | X | (aryl group with R⁵, R⁶, R¹¹) |
|----|-----|-----|-----|-----|-----|-----|
| 157 | CH₃ | CH₃ | C₂H₅ | H | —CH₂CH₂— | 2-CH₃, 4-OC₄H₉ phenyl |

TABLE 18

| No | R¹ | R² | R³ | R⁴ | X | (aryl group with R⁵, R⁶, R¹¹) |
|----|-----|-----|-----|-----|-----|-----|
| 158 | CH₃ | CH₃ | CH₃ | H | —CH₂CH₂— | 2-CH₃, 4-OC₄H₉ phenyl |
| 159 | CH₃ | C₂H₅ | CH₃ | H | —CH₂CH₂— | 2-CH₃, 4-OC₄H₉ phenyl |
| 160 | CH₃ | C₂H₅ | C₂H₅ | H | —CH₂CH₂— | 2-CH₃, 4-OC₄H₉ phenyl |
| 161 | H | C₂H₅ | CH₃ | H | —CH₂CH₂— | 2-Cl, 4-OC₄H₉ phenyl |
| 162 | H | CH₃ | CH₃ | H | —CH₂CH₂— | 2-Cl, 4-OC₄H₉ phenyl |
| 163 | H | CH₃ | C₂H₅ | H | —CH₂CH₂— | 2-Cl, 4-OC₄H₉ phenyl |
| 164 | CH₃ | CH₃ | C₂H₅ | H | —CH₂CH₂— | 2-Cl, 4-OC₄H₉ phenyl |

TABLE 18-continued

| No | R¹ | R² | R³ | R⁴ | X | Ar (R⁵, R⁶, R¹¹) |
|---|---|---|---|---|---|---|
| 165 | $CH_3$ | $CH_3$ | $CH_3$ | H | $-CH_2CH_2-$ | 2-Cl, 4-$OC_4H_9$-phenyl |
| 166 | $CH_3$ | $C_2H_5$ | $CH_3$ | H | $-CH_2CH_2-$ | 2-Cl, 4-$OC_4H_9$-phenyl |
| 167 | $CH_3$ | $C_2H_5$ | $C_2H_5$ | H | $-CH_2CH_2-$ | 2-Cl, 4-$OC_4H_9$-phenyl |

TABLE 19

| No | R¹ | R² | R³ | R⁴ | X | Ar (R⁵, R⁶, R¹¹) |
|---|---|---|---|---|---|---|
| 168 | H | $C_2H_5$ | $CH_3$ | H | $-CH_2CH_2-$ | 2-$CH_3$, 4-$OC_2H_5$-phenyl |
| 169 | H | $C_2H_5$ | $C_2H_5$ | H | $-CH_2CH_2-$ | 2-$CH_3$, 4-$OC_2H_5$-phenyl |
| 170 | H | $CH_3$ | $C_2H_5$ | H | $-CH_2CH_2-$ | 2-$CH_3$, 4-$OC_2H_5$-phenyl |
| 171 | H | $CH_3$ | $CH_3$ | H | $-CH_2CH_2-$ | 2-$CH_3$, 4-$OC_2H_5$-phenyl |
| 172 | $CH_3$ | $CH_3$ | $CH_3$ | H | $-CH_2CH_2-$ | 2-$CH_3$, 4-$OC_2H_5$-phenyl |

TABLE 19-continued

| No | R¹ | R² | R³ | R⁴ | X | aryl (R⁵, R⁶, R¹¹) |
|---|---|---|---|---|---|---|
| 173 | CH₃ | CH₃ | C₂H₅ | H | —CH₂CH₂— | 2-CH₃, 4-OC₂H₅-phenyl |
| 174 | CH₃ | C₂H₅ | CH₃ | H | —CH₂CH₂— | 2-CH₃, 4-OC₂H₅-phenyl |
| 175 | CH₃ | C₂H₅ | C₂H₅ | H | —CH₂CH₂— | 2-CH₃, 4-OC₂H₅-phenyl |
| 176 | H | C₂H₅ | C₂H₅ | H | —CH₂CH₂— | 4-OCH₂CH=CH₂-phenyl |
| 177 | H | C₂H₅ | C₂H₅ | H | —CH₂CH₂— | 4-OCH₂C≡CH-phenyl |

TABLE 20

| No | R¹ | R² | R³ | R⁴ | X | aryl (R⁵, R⁶, R¹¹) |
|---|---|---|---|---|---|---|
| 178 | H | C₂H₅ | C₂H₅ | H | —CH₂CH₂— | 4-CH=CH₂-phenyl |
| 179 | H | C₂H₅ | C₂H₅ | H | —CH₂CH₂— | 4-CH₂CH=CH₂-phenyl |
| 180 | H | C₂H₅ | C₂H₅ | H | —CH₂CH₂— | 4-CH₂CH=CHCH₃-phenyl |
| 181 | H | C₂H₅ | C₂H₅ | H | —CH₂CH₂— | 4-C≡CH-phenyl |
| 182 | H | C₂H₅ | C₂H₅ | H | —CH₂CH₂— | 4-CH₂C≡CH-phenyl |

TABLE 20-continued

Aryl group structure: phenyl with $R^5$, $R^6$, $R^{11}$ substituents

| No | $R^1$ | $R^2$ | $R^3$ | $R^4$ | X | Aryl |
|---|---|---|---|---|---|---|
| 183 | H | $C_2H_5$ | $C_2H_5$ | H | $-CH_2CH_2-$ | 4-($CH_2CH_2C\equiv CH$)-phenyl |
| 184 | H | $C_2H_5$ | $CH_2CH=CH_2$ | H | $-CH_2CH_2-$ | 4-$OC_4H_9$-phenyl |
| 185 | H | $C_2H_5$ | $CH_2C\equiv CH$ | H | $-CH_2CH_2-$ | 4-$OC_4H_9$-phenyl |
| 186 | H | $C_2H_5$ | $CH_2CH_2$-phenyl | H | $-CH_2CH_2-$ | 4-$OC_4H_9$-phenyl |
| 187 | H | $C_2H_5$ | $C_2H_5$ | H | $-CH_2CH_2-$ | 3-F, 4-$OC_4H_9$-phenyl |

TABLE 21

Aryl group structure: phenyl with $R^5$, $R^6$, $R^{11}$ substituents

| No | $R^1$ | $R^2$ | $R^3$ | $R^4$ | X | Aryl |
|---|---|---|---|---|---|---|
| 188 | H | $C_2H_5$ | $C_2H_5$ | H | $-CH_2CH_2-$ | 3-Br, 4-$OC_4H_9$-phenyl |
| 189 | H | $C_2H_5$ | $CH_3$ | H | $-CH_2CH_2-$ | 3-$CH_3$, 4-$OC_3H_7$-phenyl |
| 190 | H | $C_2H_5$ | $CH_3$ | H | $-CH_2CH_2-$ | 3-$CH_3$, 4-$OC_3H_7$-phenyl |
| 191 | H | $CH_3$ | $CH_3$ | H | $-CH_2CH_2-$ | 3-$CH_3$, 4-$OC_3H_7$-phenyl |

TABLE 21-continued

| No | R¹ | R² | R³ | R⁴ | X | Ar (R⁵, R⁶, R¹¹) |
|----|----|----|----|----|----|------------------|
| 192 | H | CH₃ | C₂H₅ | H | —CH₂CH₂— | 2-CH₃, 4-OC₃H₇-phenyl |
| 193 | CH₃ | CH₃ | C₂H₅ | H | —CH₂CH₂— | 2-CH₃, 4-OC₃H₇-phenyl |
| 194 | CH₃ | CH₃ | CH₃ | H | —CH₂CH₂— | 2-CH₃, 4-OC₃H₇-phenyl |
| 195 | CH₃ | C₂H₅ | CH₃ | H | —CH₂CH₂— | 2-CH₃, 4-OC₃H₇-phenyl |
| 196 | CH₃ | C₂H₅ | C₂H₅ | H | —CH₂CH₂— | 2-CH₃, 4-OC₃H₇-phenyl |
| 197 | H | C₂H₅ | C₂H₅ | H | —CH₂CH₂— | 2-CH₃, 4-OCH(CH₃)₂-phenyl |

TABLE 22

| No | R¹ | R² | R³ | R⁴ | X | Ar (R⁵, R⁶, R¹¹) |
|----|----|----|----|----|----|------------------|
| 198 | H | C₂H₅ | CH₃ | H | —CH₂CH₂— | 2-CH₃, 4-OCH(CH₃)₂-phenyl |
| 199 | H | CH₃ | CH₃ | H | —CH₂CH₂— | 2-CH₃, 4-OCH(CH₃)₂-phenyl |

TABLE 22-continued

| No | $R^1$ | $R^2$ | $R^3$ | $R^4$ | X | Aryl (with $R^5$, $R^6$, $R^{11}$) |
|---|---|---|---|---|---|---|
| 200 | H | $CH_3$ | $C_2H_5$ | H | $-CH_2CH_2-$ | 2-$CH_3$, 4-$OCH(CH_3)_2$ |
| 201 | $CH_3$ | $CH_3$ | $C_2H_5$ | H | $-CH_2CH_2-$ | 2-$CH_3$, 4-$OCH(CH_3)_2$ |
| 202 | $CH_3$ | $CH_3$ | $CH_3$ | H | $-CH_2CH_2-$ | 2-$CH_3$, 4-$OCH(CH_3)_2$ |
| 203 | $CH_3$ | $C_2H_5$ | $CH_3$ | H | $-CH_2CH_2-$ | 2-$CH_3$, 4-$OCH(CH_3)_2$ |
| 204 | $CH_3$ | $C_2H_5$ | $C_2H_5$ | H | $-CH_2CH_2-$ | 2-$CH_3$, 4-$OCH(CH_3)_2$ |
| 205 | H | $C_2H_5$ | $C_2H_5$ | H | $-CH_2CH_2-$ | 2-$CH_3$, 4-$OCHF_2$ |
| 206 | H | $C_2H_5$ | $CH_3$ | H | $-CH_2CH_2-$ | 2-$CH_3$, 4-$OCHF_2$ |
| 207 | H | $CH_3$ | $CH_3$ | H | $-CH_2CH_2-$ | 2-$CH_3$, 4-$OCHF_2$ |

TABLE 23

![Structure: phenyl ring with R⁵, R⁶, R¹¹ substituents]

| No | R¹ | R² | R³ | R⁴ | X | Ar group |
|----|----|----|----|----|----|----|
| 208 | H | CH₃ | C₂H₅ | H | —CH₂CH₂— | 2-CH₃, 4-OCHF₂-phenyl |
| 209 | CH₃ | CH₃ | C₂H₅ | H | —CH₂CH₂— | 2-CH₃, 4-OCHF₂-phenyl |
| 210 | CH₃ | CH₃ | CH₃ | H | —CH₂CH₂— | 2-CH₃, 4-OCHF₂-phenyl |
| 211 | CH₃ | C₂H₅ | CH₃ | H | —CH₂CH₂— | 2-CH₃, 4-OCHF₂-phenyl |
| 212 | CH₃ | C₂H₅ | C₂H₅ | H | —CH₂CH₂— | 2-CH₃, 4-OCHF₂-phenyl |
| 213 | H | C₂H₅ | C₂H₅ | H | —CH₂CH₂— | 4-I-phenyl |
| 214 | H | C₂H₅ | C₂H₅ | H | —CH₂CH₂— | 4-CH₂CH₂Cl-phenyl |
| 215 | H | C₂H₅ | C₂H₅ | H | —CH₂CH₂— | 4-CH₂OCH₃-phenyl |
| 216 | CH₃ | CH₃ | C₂H₅ | H | —CH₂CH₂— | 4-CH₂OCH₃-phenyl |
| 217 | CH₃ | CH₃ | C₂H₅ | H | —CH₂CH₂— | 4-CH₂CH₂OC₂H₅-phenyl |

TABLE 24

| No | R¹ | R² | R³ | R⁴ | X | Ar (R⁵/R⁶/R¹¹ substituted phenyl) |
|---|---|---|---|---|---|---|
| 218 | $CH_3$ | $CH_3$ | $CH_3$ | H | $-CH_2CH_2-$ | —C₆H₄—$CH_2CH_2OC_2H_5$ |
| 219 | $CH_3$ | $C_2H_5$ | $CH_3$ | H | $-CH_2CH_2-$ | —C₆H₄—$CH_2CH_2OC_2H_5$ |
| 220 | $CH_3$ | $C_2H_5$ | $C_2H_5$ | H | $-CH_2CH_2-$ | —C₆H₄—$CH_2CH_2OC_2H_5$ |
| 221 | H | $C_2H_5$ | $CH_3$ | H | $-CH_2CH_2-$ | —C₆H₄—$CH_2CH_2OC_2H_5$ |
| 222 | H | $CH_3$ | $C_2H_5$ | H | $-CH_2CH_2-$ | —C₆H₄—$CH_2CH_2OC_2H_5$ |
| 223 | H | $CH_3$ | $CH_3$ | H | $-CH_2CH_2-$ | —C₆H₄—$CH_2CH_2OC_2H_5$ |
| 224 | H | $C_2H_5$ | $C_2H_5$ | H | $-CH_2CH_2-$ | —C₆H₄—$CH_2OH$ |
| 225 | H | $CH_3$ | $C_2H_5$ | H | $-CH_2CH_2-$ | —C₆H₄—$CH_2CH_2OH$ |
| 226 | H | $C_2H_5$ | $C_2H_5$ | H | $-CH_2CH_2-$ | —C₆H₄—$CH_2OSO_2CH_3$ |
| 227 | H | $C_2H_5$ | $C_2H_5$ | H | $-CH_2CH_2-$ | —C₆H₄—$CH_2O$-(tetrahydropyran-2-yl) |

TABLE 25

| No | R¹ | R² | R³ | R⁴ | X | Ar |
|---|---|---|---|---|---|---|
| 228 | H | $CH_3$ | $C_2H_5$ | H | $-CH_2CH_2-$ | —C₆H₄—$CH_2CH_2NHCH_3$ |

TABLE 25-continued

| No | R¹ | R² | R³ | R⁴ | X | Ar group |
|---|---|---|---|---|---|---|
| 229 | H | CH₃ | C₂H₅ | H | —CH₂CH₂— | —C₆H₄—CH₂CH₂NHC₂H₅ |
| 230 | H | CH₃ | C₂H₅ | H | —CH₂CH₂— | —C₆H₄—CH₂CH₂N(CH₃)₂ |
| 231 | H | CH₃ | C₂H₅ | H | —CH₂CH₂— | —C₆H₄—CH₂CH₂N(C₂H₅)₂ |
| 232 | H | CH₃ | C₂H₅ | H | —CH₂CH₂— | —C₆H₄—CH₂CH₂SCH₃ |
| 233 | H | CH₃ | CH₃ | H | —CH₂CH₂— | —C₆H₄—CH₂CH₂SCH₃ |
| 234 | H | C₂H₅ | CH₃ | H | —CH₂CH₂— | —C₆H₄—CH₂CH₂SCH₃ |
| 235 | CH₃ | C₂H₅ | CH₃ | H | —CH₂CH₂— | —C₆H₄—CH₂CH₂SCH₃ |
| 236 | CH₃ | C₂H₅ | C₂H₅ | H | —CH₂CH₂— | —C₆H₄—CH₂CH₂SCH₃ |
| 237 | CH₃ | CH₃ | C₂H₅ | H | —CH₂CH₂— | —C₆H₄—CH₂CH₂SCH₃ |

TABLE 26

| No | R¹ | R² | R³ | R⁴ | X | Ar group |
|---|---|---|---|---|---|---|
| 238 | CH₃ | C₂H₅ | CH₃ | H | —CH₂CH₂— | —C₆H₄—CH₂CH₂SCH₃ |
| 239 | CH₃ | C₂H₅ | CH₃ | H | —CH₂CH₂— | —C₆H₄—CH₂CH₂S(=O)CH₃ |

TABLE 26-continued

| No | R¹ | R² | R³ | R⁴ | X | Aryl group with R⁵, R⁶, R¹¹ |
|---|---|---|---|---|---|---|
| 240 | CH₃ | C₂H₅ | C₂H₅ | H | —CH₂CH₂— | 4-(CH₂CH₂S(=O)CH₃)-phenyl |
| 241 | CH₃ | CH₃ | C₂H₅ | H | —CH₂CH₂— | 4-(CH₂CH₂S(=O)CH₃)-phenyl |
| 242 | CH₃ | CH₃ | CH₃ | H | —CH₂CH₂— | 4-(CH₂CH₂S(=O)CH₃)-phenyl |
| 243 | H | CH₃ | CH₃ | H | —CH₂CH₂— | 4-(CH₂CH₂S(=O)CH₃)-phenyl |
| 244 | H | CH₃ | C₂H₅ | H | —CH₂CH₂— | 4-(CH₂CH₂S(=O)CH₃)-phenyl |
| 245 | H | C₂H₅ | CH₃ | H | —CH₂CH₂— | 4-(CH₂CH₂S(=O)CH₃)-phenyl |
| 246 | H | C₂H₅ | CH₃ | H | —CH₂CH₂— | 4-(OCH₂CH₂SCH₃)-phenyl |
| 247 | H | CH₃ | CH₃ | H | —CH₂CH₂— | 4-(OCH₂CH₂SCH₃)-phenyl |

TABLE 27

| No | R¹ | R² | R³ | R⁴ | X | Aryl group with R⁵, R⁶, R¹¹ |
|---|---|---|---|---|---|---|
| 248 | H | CH₃ | C₂H₅ | H | —CH₂CH₂— | 4-(OCH₂CH₂SCH₃)-phenyl |
| 249 | H | C₂H₅ | C₂H₅ | H | —CH₂CH₂— | 4-(CH₂S(=O)C₂H₅)-phenyl |

TABLE 27-continued

| No | R¹ | R² | R³ | R⁴ | X | Ar (R⁵, R⁶, R¹¹) |
|---|---|---|---|---|---|---|
| 250 | H | C₂H₅ | C₂H₅ | H | —CH₂CH₂— | -C₆H₄-CH₂SO₂C₂H₅ |
| 251 | H | C₂H₅ | C₂H₅ | H | —CH₂CH₂— | -C₆H₄-CH₂CH₂SO₂CH₃ |
| 252 | H | C₂H₅ | C₂H₅ | H | —CH₂CH₂— | -C₆H₄-OCH₂CH₂Cl |
| 253 | H | C₂H₅ | C₂H₅ | H | —CH₂CH₂— | -C₆H₄-OCH₂OC₂H₅ |
| 254 | H | C₂H₅ | C₂H₅ | H | —CH₂CH₂— | -C₆H₄-OCH₂SC₂H₅ |
| 255 | H | C₂H₅ | CH₃ | H | —CH₂CH₂— | -C₆H₄-OCH₂CH₂S(O)CH₃ |
| 256 | H | CH₃ | CH₃ | H | —CH₂CH₂— | -C₆H₄-OCH₂CH₂S(O)CH₃ |
| 257 | H | CH₃ | C₂H₅ | H | —CH₂CH₂— | -C₆H₄-OCH₂CH₂S(O)CH₃ |

TABLE 28

| No | R¹ | R² | R³ | R⁴ | X | Ar (R⁵, R⁶, R¹¹) |
|---|---|---|---|---|---|---|
| 258 | CH₃ | CH₃ | C₂H₅ | H | —CH₂CH₂— | -C₆H₄-OCH₂CH₂S(O)CH₃ |
| 259 | CH₃ | CH₃ | CH₃ | H | —CH₂CH₂— | -C₆H₄-OCH₂CH₂S(O)CH₃ |

TABLE 28-continued

| No | R¹ | R² | R³ | R⁴ | X | Ar (R⁵, R⁶, R¹¹) |
|---|---|---|---|---|---|---|
| 260 | $CH_3$ | $C_2H_5$ | $CH_3$ | H | $-CH_2CH_2-$ | -C₆H₄-OCH₂CH₂S(O)CH₃ |
| 261 | $CH_3$ | $C_2H_5$ | $C_2H_5$ | H | $-CH_2CH_2-$ | -C₆H₄-OCH₂CH₂S(O)CH₃ |
| 262 | $CH_3$ | $C_2H_5$ | $C_2H_5$ | H | $-CH_2CH_2-$ | -C₆H₄-OCH₂CH₂SCH₃ |
| 263 | $CH_3$ | $C_2H_5$ | $CH_3$ | H | $-CH_2CH_2-$ | -C₆H₄-OCH₂CH₂SCH₃ |
| 264 | $CH_3$ | $CH_3$ | $CH_3$ | H | $-CH_2CH_2-$ | -C₆H₄-OCH₂CH₂SCH₃ |
| 265 | $CH_3$ | $CH_3$ | $C_2H_5$ | H | $-CH_2CH_2-$ | -C₆H₄-OCH₂CH₂SCH₃ |
| 266 | H | $CH_3$ | $C_2H_5$ | H | $-CH_2CH_2-$ | -C₆H₄-OCH₂CH₂S(O)₂CH₃ |
| 267 | H | $CH_3$ | $CH_3$ | H | $-CH_2CH_2-$ | -C₆H₄-OCH₂CH₂S(O)₂CH₃ |

TABLE 29

| No | R¹ | R² | R³ | R⁴ | X | Ar (R⁵, R⁶, R¹¹) |
|---|---|---|---|---|---|---|
| 268 | $CH_3$ | $C_2H_5$ | $CH_3$ | H | $-CH_2CH_2-$ | -C₆H₄-OCH₂CH₂S(O)₂CH₃ |
| 269 | $CH_3$ | $CH_3$ | $C_2H_5$ | H | $-CH_2CH_2-$ | -C₆H₄-OCH₂CH₂S(O)₂CH₃ |
| 270 | H | $C_2H_5$ | $C_2H_5$ | H | $-CH_2CH_2-$ | -C₆H₄-OCH₂CH₂N(CH₃)₂ |

TABLE 29-continued

| No | R¹ | R² | R³ | R⁴ | X | Ar (R⁵, R⁶, R¹¹ substituted phenyl) |
|---|---|---|---|---|---|---|
| 271 | H | C₂H₅ | C₂H₅ | H | —CH₂CH₂— | 4-(phenoxy)phenyl |
| 272 | CH₃ | CH₃ | C₂H₅ | H | —CH₂CH₂— | 4-(phenoxy)phenyl |
| 273 | CH₃ | CH₃ | C₂H₅ | H | —CH₂CH₂— | 4-(4-fluorophenoxy)phenyl |
| 274 | CH₃ | C₂H₅ | C₂H₅ | H | —CH₂CH₂— | 4-(4-fluorophenoxy)phenyl |
| 275 | H | CH₃ | C₂H₅ | H | —CH₂CH₂— | 4-(4-fluorophenoxy)phenyl |
| 276 | H | C₂H₅ | C₂H₅ | H | —CH₂CH₂— | 4-(SCH₃)phenyl |
| 277 | H | C₂H₅ | C₂H₅ | H | —CH₂CH₂— | 4-(SC₂H₅)phenyl |

TABLE 30

| No | R¹ | R² | R³ | R⁴ | X | Ar (R⁵, R⁶, R¹¹ substituted phenyl) |
|---|---|---|---|---|---|---|
| 278 | H | C₂H₅ | C₂H₅ | H | —CH₂CH₂— | 4-(SC₃H₇)phenyl |
| 279 | H | C₂H₅ | C₂H₅ | H | —CH₂CH₂— | 4-(SCH(CH₃)₂)phenyl |
| 280 | H | C₂H₅ | C₂H₅ | H | —CH₂CH₂— | 4-(S(O)CH₃)phenyl |
| 281 | H | C₂H₅ | C₂H₅ | H | —CH₂CH₂— | 4-(S(O)C₂H₅)phenyl |

TABLE 30-continued

| No | R¹ | R² | R³ | R⁴ | X | Aryl group (R⁵, R⁶, R¹¹) |
|---|---|---|---|---|---|---|
| 282 | H | $C_2H_5$ | $C_2H_5$ | H | $-CH_2CH_2-$ | 4-$S(O)C_3H_7$-phenyl |
| 283 | H | $C_2H_5$ | $C_2H_5$ | H | $-CH_2CH_2-$ | 4-$S(O)_2CH_3$-phenyl |
| 284 | H | $C_2H_5$ | $C_2H_5$ | H | $-CH_2CH_2-$ | 4-$S(O)_2C_2H_5$-phenyl |
| 285 | H | $C_2H_5$ | $C_2H_5$ | H | $-CH_2CH_2-$ | 4-$S(O)_2C_3H_7$-phenyl |
| 286 | H | $C_2H_5$ | $CH_3$ | H | $-CH_2CH_2-$ | 3-Cl-4-$OC_2H_5$-phenyl |
| 287 | H | $C_2H_5$ | $C_2H_5$ | H | $-CH_2CH_2-$ | 3-Cl-4-$OC_2H_5$-phenyl |

TABLE 31

| No | R¹ | R² | R³ | R⁴ | X | Aryl group (R⁵, R⁶, R¹¹) |
|---|---|---|---|---|---|---|
| 288 | H | $CH_3$ | $C_2H_5$ | H | $-CH_2CH_2-$ | 3-Cl-4-$OC_2H_5$-phenyl |
| 289 | H | $CH_3$ | $CH_3$ | H | $-CH_2CH_2-$ | 3-Cl-4-$OC_2H_5$-phenyl |
| 290 | $CH_3$ | $CH_3$ | $CH_3$ | H | $-CH_2CH_2-$ | 3-Cl-4-$OC_2H_5$-phenyl |

TABLE 31-continued

| No | R¹ | R² | R³ | R⁴ | X | (aryl with R⁵, R⁶, R¹¹) |
|---|---|---|---|---|---|---|
| 291 | CH₃ | CH₃ | C₂H₅ | H | —CH₂CH₂— | 3-Cl, 4-OC₂H₅ |
| 292 | CH₃ | C₂H₅ | C₂H₅ | H | —CH₂CH₂— | 3-Cl, 4-OC₂H₅ |
| 293 | CH₃ | C₂H₅ | CH₃ | H | —CH₂CH₂— | 3-Cl, 4-OC₂H₅ |
| 294 | H | C₂H₅ | CH₃ | H | —CH₂CH₂— | 3-Cl, 4-OC₃H₇ |
| 295 | H | C₂H₅ | C₂H₅ | H | —CH₂CH₂— | 3-Cl, 4-OC₃H₇ |
| 296 | H | CH₃ | C₂H₅ | H | —CH₂CH₂— | 3-Cl, 4-OC₃H₇ |
| 297 | H | CH₃ | CH₃ | H | —CH₂CH₂— | 3-Cl, 4-OC₃H₇ |

TABLE 32

| No | R¹ | R² | R³ | R⁴ | X | (aryl with R⁵, R⁶, R¹¹) |
|---|---|---|---|---|---|---|
| 298 | CH₃ | CH₃ | CH₃ | H | —CH₂CH₂— | 3-Cl, 4-OC₃H₇ |

TABLE 32-continued

| No | R¹ | R² | R³ | R⁴ | X | Aryl (R⁵, R⁶, R¹¹) |
|---|---|---|---|---|---|---|
| 299 | CH₃ | CH₃ | C₂H₅ | H | —CH₂CH₂— | 2-Cl, 4-OC₃H₇ phenyl |
| 300 | CH₃ | C₂H₅ | C₂H₅ | H | —CH₂CH₂— | 2-Cl, 4-OC₃H₇ phenyl |
| 301 | CH₃ | C₂H₅ | CH₃ | H | —CH₂CH₂— | 2-Cl, 4-OC₃H₇ phenyl |
| 302 | H | CH₃ | C₂H₅ | H | —CH₂CH₂— | 2-Cl, 4-OCH(CH₃)₂ phenyl |
| 303 | H | CH₃ | CH₃ | H | —CH₂CH₂— | 2-Cl, 4-OCH(CH₃)₂ phenyl |
| 304 | H | C₂H₅ | CH₃ | H | —CH₂CH₂— | 2-Cl, 4-OCH(CH₃)₂ phenyl |
| 305 | H | C₂H₅ | C₂H₅ | H | —CH₂CH₂— | 2-Cl, 4-OCH(CH₃)₂ phenyl |
| 306 | CH₃ | C₂H₅ | C₂H₅ | H | —CH₂CH₂— | 2-Cl, 4-OCH(CH₃)₂ phenyl |
| 307 | CH₃ | C₂H₅ | CH₃ | H | —CH₂CH₂— | 2-Cl, 4-OCH(CH₃)₂ phenyl |

TABLE 33

| No | R¹ | R² | R³ | R⁴ | X | Ar (R⁵, R⁶, R¹¹ substituted phenyl) |
|---|---|---|---|---|---|---|
| 308 | $CH_3$ | $CH_3$ | $CH_3$ | H | $-CH_2CH_2-$ | 3-Cl, 4-$OCH(CH_3)_2$-phenyl |
| 309 | $CH_3$ | $CH_3$ | $C_2H_5$ | H | $-CH_2CH_2-$ | 3-Cl, 4-$OCH(CH_3)_2$-phenyl |
| 310 | $CH_3$ | $CH_3$ | $C_2H_5$ | H | $-CH_2CH_2-$ | 3-Cl, 4-$OCHF_2$-phenyl |
| 311 | $CH_3$ | $CH_3$ | $CH_3$ | H | $-CH_2CH_2-$ | 3-Cl, 4-$OCHF_2$-phenyl |
| 312 | $CH_3$ | $C_2H_5$ | $CH_3$ | H | $-CH_2CH_2-$ | 3-Cl, 4-$OCHF_2$-phenyl |
| 313 | $CH_3$ | $C_2H_5$ | $C_2H_5$ | H | $-CH_2CH_2-$ | 3-Cl, 4-$OCHF_2$-phenyl |
| 314 | H | $C_2H_5$ | $C_2H_5$ | H | $-CH_2CH_2-$ | 3-Cl, 4-$OCHF_2$-phenyl |
| 315 | H | $C_2H_5$ | $CH_3$ | H | $-CH_2CH_2-$ | 3-Cl, 4-$OCHF_2$-phenyl |
| 316 | H | $CH_3$ | $CH_3$ | H | $-CH_2CH_2-$ | 3-Cl, 4-$OCHF_2$-phenyl |

TABLE 33-continued

| No | R¹ | R² | R³ | R⁴ | X | (aryl with R⁵, R⁶, R¹¹) |
|----|----|----|----|----|----|----|
| 317 | H | CH₃ | C₂H₅ | H | —CH₂CH₂— | 3-Cl, 4-OCHF₂-phenyl |

TABLE 34

| No | R¹ | R² | R³ | R⁴ | X | (aryl with R⁵, R⁶, R¹¹) |
|----|----|----|----|----|----|----|
| 318 | H | C₂H₅ | CH₃ | H | —CH₂CH₂— | 3-Cl, 4-OC₄H₉-phenyl |
| 319 | H | CH₃ | CH₃ | H | —CH₂CH₂— | 3-Cl, 4-OC₄H₉-phenyl |
| 320 | CH₃ | CH₃ | CH₃ | H | —CH₂CH₂— | 3-Cl, 4-OC₄H₉-phenyl |
| 321 | CH₃ | CH₃ | C₂H₅ | H | —CH₂CH₂— | 3-Cl, 4-OC₄H₉-phenyl |
| 322 | CH₃ | C₂H₅ | C₂H₅ | H | —CH₂CH₂— | 3-Cl, 4-OC₄H₉-phenyl |
| 323 | CH₃ | C₂H₅ | CH₃ | H | —CH₂CH₂— | 3-Cl, 4-OC₄H₉-phenyl |
| 324 | H | C₂H₅ | C₂H₅ | H | —CH(CH₃)— | 4-OCHF₂-phenyl |

TABLE 34-continued

| No | R¹ | R² | R³ | R⁴ | X | (phenyl with R⁵, R⁶, R¹¹) |
|---|---|---|---|---|---|---|
| 325 | H | $C_2H_5$ | $C_2H_5$ | H | $-\underset{C_2H_5}{\overset{}{CH}}-$ | —⟨phenyl⟩—$OCHF_2$ |
| 326 | H | $CH_3$ | $C_2H_5$ | H | $-CH_2CH_2-$ | —⟨phenyl⟩—$OCH_2CH_2OC_2H_5$ |
| 327 | $CH_3$ | $CH_3$ | $C_2H_5$ | H | $-CH_2CH_2-$ | —⟨phenyl⟩—$OCH_2CH_2OC_2H_5$ |

Among these aminopyrimidine compounds of the formula (I), the following compounds are particularly preferred:

Ethyl 4-(2-(4-difluoromethoxyphenyl)ethylamino)-6-ethylpyrimidine-5-carboxylate (Compound No. 76), Ethyl 4-(2-(4-butoxy-3-methyl phenyl)ethylamino)-6-ethylpyrimidine-5-carboxylate (Compound No. 24), Ethyl 4-(2-(4-propoxyphenyl)ethylamino)-6-ethylpyrimidine-5-carboxylate (Compound No. 18), Ethyl 4-(2-(4-butoxyphenyl)ethylamino)-6-methylpyrimidine-5-carboxylate (Compound No. 8), Ethyl 4-(2-(4-butylphenyl)ethylamino)-6-ethylpyrimidine-5-carboxylate (Compound No. 47), Ethyl 4-(2-(4-butoxyphenyl)ethylamino)-6-ethylpyrimidine-5-carboxylate (Compound No. 3), and Ethyl 4-(2-(4-ethoxyethylphenyl)ethylamino)-6-ethylpyrimidine-5-carboxyl ate (Compound No. 20).

The aminopyrimidine derivative (I) of the present invention can be prepared, for example, according to the following scheme by condensation of the compound (II) and the amine compound (III) in an appropriate solvent in the presence or absence of a base.

Examples of each group represented by $R^{3'}$ include same groups as those represented by $R^3$.

The amount of the amine compound (III) to be used is 1 to 2 mol per mol of the compound (II).

Examples of the solvent include alcohols (e.g., methanol, ethanol, propanol, isopropanol, butanol, etc.), ethers (e.g., diethyl ether, tetrahydrofuran, etc.), N,N-dimethylformamide, dimethyl sulfoxide, aromatic hydrocarbons (e.g., toluene, xylene, etc.), halogenated hydrocarbons (e.g., methylene chloride, etc.), ketones (e.g., acetone, ethyl methyl ketone, etc.), water and the like. These solvents can be used alone or as mixed solvents thereof.

Examples of the base include organic bases such as triethylamine, pyridine N,N-dimethylaniline, N,N-diethylaniline and the like; inorganic bases such as sodium hydroxide, potassium hydroxide, Calcium hydroxide, sodium carbonate, potassium carbonate and the like. The amount of the base to be used is 1 to 3 mol per mol of the compound (II).

The reaction temperature is room temperature to reflux temperature. The reaction time is 1 to 24 hours.

The compound (I) thus obtained can be separated and purified by known methods.

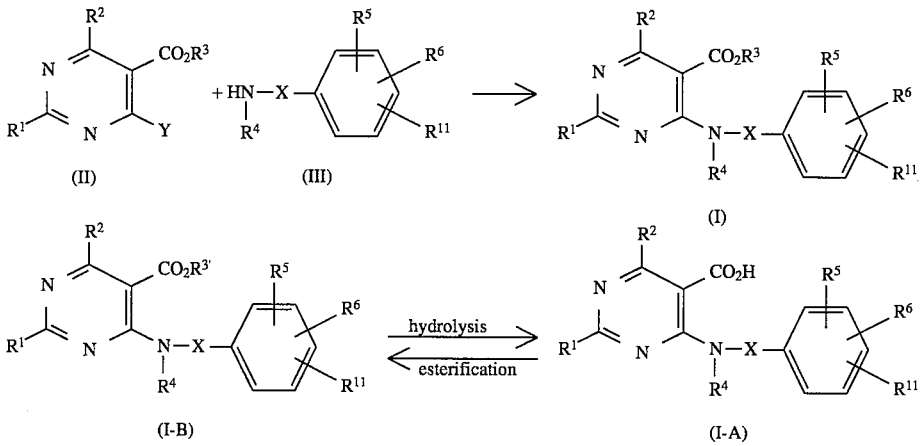

wherein Y is a halogen atom (e.g., fluorine, chlorine, bromine, iodine); $R^{3'}$ is alkyl, alkenyl, alkynyl or aralkyl; and the other symbols are as defined for the formula (I).

The compound (I) thus obtained can optionally be converted into the carboxylic acid derivative (I-A) by hydrolyzing the $-CO_2R^3$ group, or into the ester (I-B) by esterifying the carboxylic acid derivative (I-A).

For example, the ester (I-B) can be converted into the carboxylic acid derivative (I-A) by hydrolysis in an appropriate solvent in the presence of a base.

As the solvent, there can be used mixtures of an alcohol (e.g., methanol, ethanol, propanol, isopropanol, butanol, etc.) and an appropriate amount of water.

Examples of the base include inorganic bases such as lithium hydroxide, sodium hydroxide, potassium hydroxide, calcium hydroxide, sodium carbonate, potassium carbonate and the like. The amount of the base to be used is 1 to 5 mol per mol of the ester (I-B).

The reaction temperature is room temperature to reflux temperature. The reaction time is 1 to 24 hours.

The carboxylic acid derivative (I-A) can be separated and purified by conventional methods.

The carboxylic acid derivative (I-A) can be converted into the ester (I-B) by esterification according to the following three methods.

(1) Method wherein the carboxylic acid derivative (I-A) is reacted with an alkyl halide or aralkyl halide in an appropriate solvent in the presence of a base:

Examples of the alkyl halide include methyl iodide, ethyl iodide, methyl bromide, ethyl bromide and the like. Examples of the aralkyl halide include benzyl iodide, benzyl bromide and the like.

Examples of the solvent include ethers (e.g., diethyl ether, tetrahydrofuran, etc.), ketches (e.g., acetone, ethyl methyl ketone, etc.), N,N-dimethylformamide, dimethyl sulfoxide, aromatic hydrocarbons (e.g., toluene, xylene, etc.) and the like.

Examples of the base include inorganic bases such as sodium carbonate, calcium carbonate, sodium hydroxide, potassium hydroxide and the like. The amount of the base to be used is 1 to 2 mol per mol of the carboxylic acid derivative (I-A).

The reaction temperature is room temperature to reflux temperature. The reaction time is 1 to 24 hours.

(2) Method wherein the carboxylic acid derivative (I-A) is reacted with a dialkyl sulfate in an appropriate solvent in the presence of a base:

Examples of the dialkyl sulfate include dimethyl sulfate, diethyl sulfate and the like.

Examples of the solvent include ethers (e.g., diethyl ether, tetrahydrofuran, etc.), N,N-dimethylformamide, dimethyl sulfoxide, aromatic hydrocarbons (e.g., toluene, xylene, etc.), halogenated hydrocarbons (e.g., methylene chloride, etc.), ketones (e.g., acetone, ethyl methyl ketone, etc.) and the like.

Examples of the base include inorganic bases such as sodium carbonate, potassium carbonate, sodium hydroxide, potassium hydroxide and the like. The amount of the base to be used is 1 to 3 mol per mol of the carboxylic acid derivative (I-A).

The reaction temperature is room temperature to reflux temperature. The reaction time is 1 to 24 hours.

(3) Method wherein the carboxylic acid derivative (I-A) is reacted with an alcohol in the presence of an acid:

Examples of the alcohol include methanol, ethanol, propanol, isopropanol, butanol, benzyl alcohol and the like.

Examples of the acid include inorganic acids such as hydrochloric acid, sulfuric acid, phosphoric acid and the like; organic acids such as p-toluenesulfonic acid and the like. The amount of the acid to be used is 0.05 to 1 mol per mol of the carboxylic acid derivative (I-A).

The reaction is performed at room temperature to reflux temperature for 1 to 24 hours while removing the resulting water.

The ester (I-B) thus obtained can be separated and purified by conventional methods.

The amine compound (III) used in the above reaction can be prepared from the corresponding alcohol or ketone by known methods (J. Am. Chem. Soc., 76, 4180 (1954) or Angew. Chem., 80, 986 (1968)).

On the other hand, the compound (II) used in the above reaction can preferably be prepared according to the following scheme by halogenating the compound (IV) with an appropriate halogenating agent in the absence of solvents or in toluene.

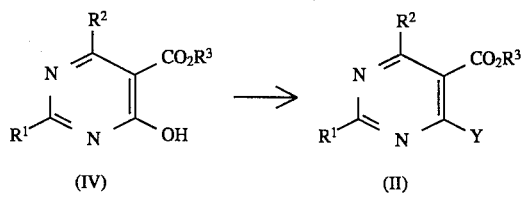

(IV)     (II)

wherein Y is a halogen atom and the other symbols are as defined for the formula (I).

Examples of the halogenating agent include phosphorus oxychloride, phosphorus pentachloride, phosphorus pentabromide, thionyl bromide or thionyl chloride. The amount of the halogenating agent to be used is 1 to 5 mol per mol of the compound (IV). The reaction temperature is room temperature to reflux temperature of the solvent. The reaction temperature is 1 to 24 hours.

The compound (II) thus obtained can be used for the preparation of the compound (I), if necessary after separation and purification by conventional methods.

The compound (II) is a novel compound. The present invention also provides this novel compound useful as an intermediate for the production of the compound (I). When the compound (II) has an asymmetric carbon atom, each optical isomer and racemic mixtures are also included in the scope of the present invention. The compound (II) is preferably that wherein Y is a chlorine atom, provided that $R^1$ is other than a halogen atom or optionally substituted phenyl.

The compound (IV) used in the above preparation of the compound (II) can preferably be prepared according to the following scheme by condensing the compound (V) with the amidine compound (VI) or an acid (e.g., acetic acid, hydrogen chloride, ½ sulfuric acid, etc.) addition salt thereof in the presence or absence of a base.

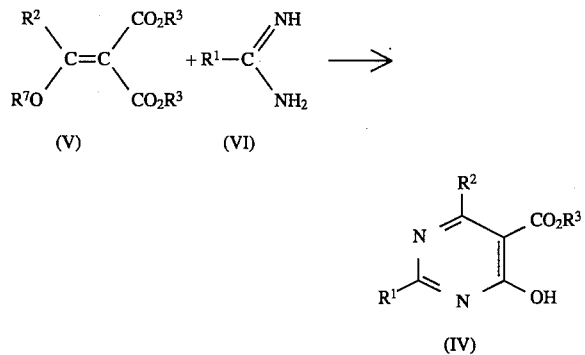

wherein $R^7$ is $C_{1-4}$ alkyl (e.g., methyl, ethyl, propyl, etc.), $C_{1-4}$ alkyl-carbonyl (e.g., methylcarbonyl, ethylcarbonyl, etc.), $C_{1-4}$ alkylsulfonyl (e.g., methylsulfonyl, ethylsulfonyl, etc.), and the other symbols are as defined for the formula (I).

The amount of the amidine compound (VI) to be used is 1 to 2 mol per mol of the compound (V).

Examples of the solvent include alcohols (e.g., methanol, ethanol, propanol, isopropanol, n-butanol, tert-butanol, etc.), ethers (e.g., diethyl ether, tetrahydrofuran, etc.), N,N-dimethylformamide, dimethyl sulfoxide, aromatic hydrocarbons (e.g, toluene, xylene, etc.), halogenated hydrocarbons (e.g., methylene chloride, etc.), ketones (e.g., acetone, ethyl methyl ketone, etc.), water and the like. These solvents can be used alone or as mixed solvents thereof.

Examples of the base include organic bases such as triethylamine, pyridine, N,N-dimethylaniline, N,N-diethylaniline, sodium methoxide, sodium ethoxide, potassium tert-butoxide and the like; inorganic bases such as sodium hydroxide, potassium hydroxide, calcium hydroxide, sodium carbonate, potassium carbonate and the like. The amount of the base to be used is 1 to 3 mol per mol of the compound (V).

The reaction temperature is −20° C. to reflux temperature. The reaction time is 1 to 24 hours.

The compound (IV) thus obtained can be used for the preparation of the above compound (II), if necessary after separation and purification by conventional methods.

The compound (IV) is a novel compound. The present invention also provides this novel compound useful as an intermediate for the production of the compound (I). When the compound (IV) has an asymmetric carbon atom, each optical isomer and racemic mixtures thereof are also included in the scope of the present invention.

The above compound (V) can be prepared according the method described in J. Org. Chem., 50, 2622 (1985) or JP-A 3-109354.

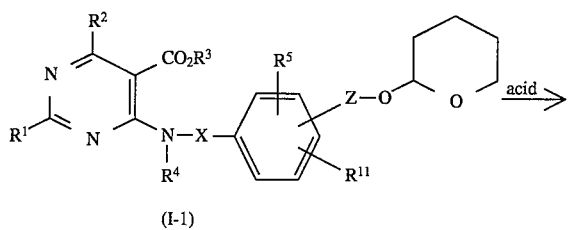

wherein $R^7$ is as defined for the formula (V), and the other symbols are as defined for the formula (I).

Various derivatives of the 4-aminopyrimidine compound (I) of the present invention can also be obtained by modifying the group corresponding to $R^6$ of the formula (I) to give the compounds (I-1), (I-2), (I-3), (I-4) and (I-5).

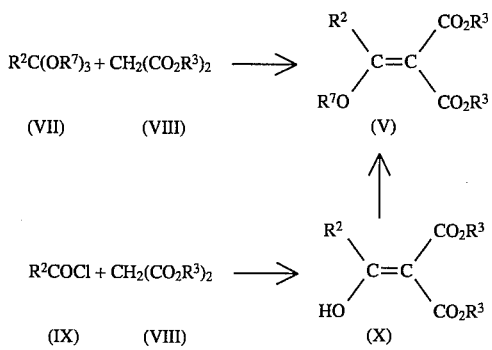

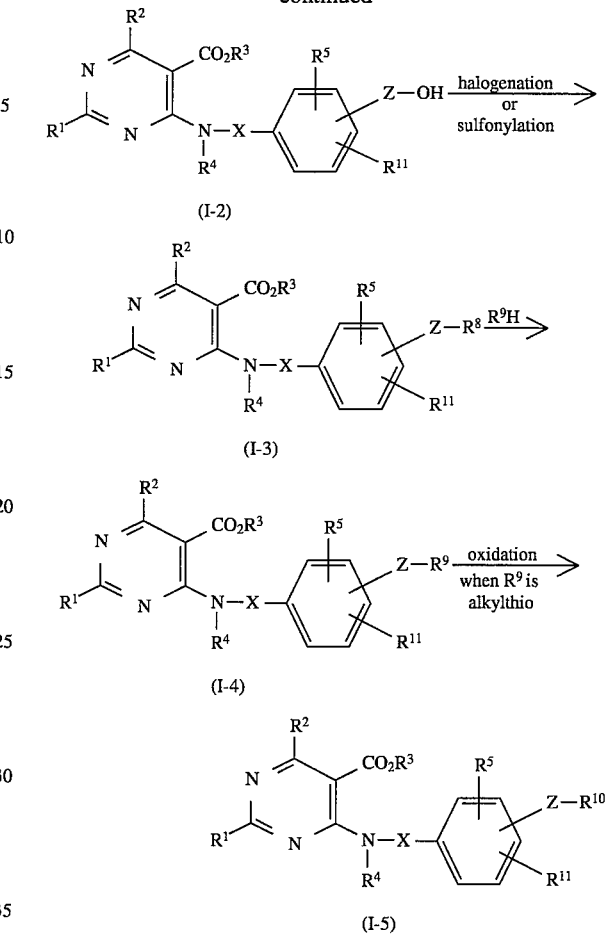

wherein Z is as defined for X; $R^6$ is a halogen atom (e.g., fluorine, chlorine, bromine, iodine), alkylsulfonyloxy (e.g., methylsulfonyloxy, ethylsulfonyloxy, etc.) or arylsulfonyloxy (e.g., p-toluenesulfonyloxy, etc.); $R^6$ is mono- or dialkylamino (e.g., methylamino, diethylamino, etc.) or alkylthio (e.g., methylthio, ethylthio, etc.); $R^{10}$ is alkylsulfinyl (e.g., methylsulfinyl, ethylsulfinyl, etc.) or alkylsulfonyl (e.g., methylsulfonyl, ethylsulfonyl, etc.); and the other symbols are as defined for the formula (I).

The compound (I-1) (i.e., the compound (I) wherein $R^6$ is tetrahydropyran-2-yloxyalkyl, or tetrahydropyran-2-yloxyalkoxy) is reacted in an alcohol in the presence of an acid (e.g., p-toluenesulfonic acid, hydrochloric acid, etc.) to give the alcohol (I-2). The reaction temperature is room temperature to reflux temperature of the solvent. The reaction time is 20 minutes to 24 hours. If necessary, the compound (I-2) thus obtained can be separated and purified by conventional methods.

Then, the compound (I-2) is reacted with a halogenating agent or sulfonating agent in an appropriate solvent in the presence or absence of a base to give the compound (I- 3). Examples of the solvent include halogenated hydrocarbons, ethers or aromatic hydrocarbons. As the base, there can be used, for example, triethylamine, N,N-dimethylaniline, N,N-diethylaniline or pyridine in an amount of 1 to 3 mol per mol of the compound (I-2). As the halogenating agent, there can be used, for example, thionyl chloride, thionyl bromide or phosphorus tribromide in an amount of 1 to 2 mol per mol of the compound (I-2). As the sulfonating agent, there can be used, for example, methanesulfonyl chloride or p-toluenesulfonyl chloride in an amount of 1 to 2 mol per mol of the compound (I-2). The reaction temperature is 0° to reflux temperature of the solvent. The reaction time is 30 minutes to 24 hours. If necessary, the compound (I-3) thus obtained can be separated and purified by conventional methods.

Then, the compound (I-3) is reacted with mono- or dialkylamine or alkyl mercaptan in an appropriate solvent in the presence or absence of a base to give the compound (I-4). The amount of the mono- or dialkylamine or alkyl mercaptan to be used is 1 to 5 mol per mol of the compound (I-3). Examples of the solvent include halogenated hydrocarbons, ethers, aromatic hydrocarbons, acetonitrile, N,N-dimethylformamide, dimethyl sulfoxide and the like. As the base, there can be used, for example, sodium carbonate, potassium carbonate, sodium hydroxide, potassium hydroxide, sodium hydride, potassium hydride or the like in an amount of 1 to 3 mol per mol of the mono- or dialkyl amine or alkyl mercaptan. The reaction temperature is room temperature to reflux temperature of the solvent. The reaction time is 1 to 24 hours. If necessary, The compound (I-4) thus obtained can be separated and purified by conventional methods.

Then, the compound (I-4) is reacted with m-chloroperbenzoic acid in a halogenated hydrocarbon to give the compound (I-5). The amount of the m-chloroperbenzoic acid to be used is 1 to 3 mol per mol of the compound (I-4). The reaction temperature is −20° to room temperature. The reaction time is 30 minutes to 24 hours. If necessary, the compound (I-5) thus obtained can be separated and purified by conventional methods.

The aminopyrimidine compounds of the present invention show high fungicidal activities against a wide variety of pathogens on crop plants (e.g., rice, wheat, barley, rye, corn, common millet, millet, buckwheat, soybean, redbean, peanut, cucumber, eggplant, tomato, pumpkin, kidney bean, citrus fruits, grape, apple, pear, peach, etc.) and the like. Specific examples of the pathogen include *Pyricularia oryzae, Rhizoctonia solani, Erysiphe graminis, Sphaerotheca fuliginea, Erysiphe cichoracearum, Phytophthora infestans, Pseudoperonospora cubensis, Peronospora manshurica, Plasmopara viticola, Botrytis cinerea* of vegetables, grape and the like, *Pythium aphanidermatum, Sclerotinia sclerotiorum* of buckwheat, soybean, colza and the like, *Corticium rolfsii* of soybean, redbean, potato, peanut and the like. Therefore, the aminopyrimidine compounds of the present invention are useful as agricultural fungicides.

Further, the aminopyrimidine compounds of the present invention show excellent insecticidal activity against aphides (e.g., *Myzus persicae*, etc.), planthoppers, leafhoppers (e.g., *Nephotettix cincticeps*, etc.) and the like. Further, they show excellent miticidal activity against various spider mites (e.g., *Tetranychus urticae, Tetranychus kanzawai, Panonychus citri*, etc.). Therefore, aminopyrimidine compounds of the invention are also useful as insecticides and miticides.

When the aminopyrimidine compounds of the present invention are used as agricultural fungicides, they can be applied to plants by any conventional manner such as atomizing, scattering, spreading or the like. Application may also be made to seeds of plants, soil around plants, soil to be seeded, paddies, water of hydroponic culture or the like. Application can be made before or after the infection of plants with pathogens.

When the aminopyrimidine compounds of the present invention are used as insecticides or miticides, they can be applied to insects or spider mites by any conventional manner such as atomizing, scattering, spreading or the like. They may also be applied to plants by any conventional manner such as atomizing, scattering, spreading or the like to prevent damage caused by pests. Further, application may also be made to seeds of plants, soil around plants, soil to be seeded, paddies or the like.

The aminopyrimidine compounds of the present invention can be used in the form of a conventional composition or preparation suitable for agricultural fungicides, insecticides or miticides such as solutions, wettable powders, emulsions, suspensions, concentrated liquid preparations, tablets, granules, aerosols, powders, pastes, dusts or the like. These compositions or preparations can be obtained by conventional methods, for example, by mixing at least one of the aminopyrimidine compounds with an agriculturally acceptable solid or liquid carrier and, if necessary, an appropriate adjuvant (e.g., surfactant, spreader, disperser, stabilizer, etc.) for improvement of dispersibility and other properties of the effective component.

Examples of the solid carrier or diluent include botanical materials (e.g., flour, tobacco stalk powder, soybean powder, walnut-shell powder, vegetable powder, saw dust, bran, bark powder, cellulose powder, vegetable extract residue, etc.), fibrous materials (e.g., paper, corrugated cardboard, old rags, etc.), artificial plastic powders, clays (e.g., kaolin, bentonite, fuller's earth, etc.), talc, other inorganic materials (e.g., pyrophyllite, sericite, pumice, sulfur powder, active carbon, etc.), chemical fertilizers (e.g., ammonium sulfate, ammonium phosphate, ammonium nitrate, urea, ammonium chloride, etc.) and the like.

Examples of the liquid carrier or diluent include water, alcohols (e.g., methanol, ethanol, etc.), ketones (e.g., acetone, ethyl methyl ketone, etc.), ethers (e.g., diethyl ether, dioxane, cellosolve, tetrahydrofuran, etc.), aromatic hydrocarbons (e.g., benzene, toluene, xylene, methylnaphthalene, etc.), aliphatic hydrocarbons (e.g., gasoline, kerosene, lamp oil, etc.), esters, nitriles, acid amides (e.g., N,N-dimethylformamide, N,N-dimethylacetamide, etc.), halogenated hydrocarbons (e.g., dichloroethane, carbon tetrachloride, etc.) and the like.

Examples of the surfactant include alkyl sulfates, alkyl sulfonates, alkylaryl sulfonates, polyethylene glycol ethers, polyhydric alcohol esters and the like.

Examples of the spreader or disperser include casein, gelatin, starch powder, carboxymethyl cellulose, gum arabic, alginic acid, lignin, bentonite, molasses, polyvinyl alcohol, pine oil, agar and the like.

Examples of the stabilizer include PAP (a mixture of isopropylphosphate), tricresyl phosphate (TCP), tolu oil, epoxidized oil, surfactants, fatty acids and their esters and the like.

The composition of the present invention may contain other fungicides, insecticides, herbicides, fertilizers and the like in addition to the above components.

When the aminopyrimidine compounds are used as agricultural fungicides, insecticides or miticides, each of such compositions contains at least one of the aminopyrimidine compounds in a concentration of normally 0.1 to 99% by weight, preferably 1 to 60% by weight. The compositions can be used as such or in a diluted form. The concentration to be used depends upon a particular purpose, subject and plant to be treated, and it is generally in the range of about 1 to 5,000 ppm. The amount of the active component to be used is generally 1.0 g to 5 kg per hectare.

As described hereinabove, according to the present invention, there are provided novel aminopyrimidine compounds, processes for producing them, intermediates for the production, and agricultural fungicides, insecticides and miticides containing them as active components.

The following examples and experiments further illustrate the present invention in detail, but are not to be construed to limit the scope thereof. The spin coupling constants (J) in the NMR data are indicated in terms of Hz.

EXAMPLE 1

Synthesis of Ethyl 6-Ethyl-4-hydroxypyrimidine-5-carboxylate (Compound No. IV-5)

A solution of ethyl 2-carboethoxy-3-methoxy-2-pentenoate (11.00 g, 47.77 mmol) in ethanol (40 ml) was stirred under ice-cooling. To the mixture was added a formamidine acetic acid salt (5.96 g, 57.25 mmol), followed by addition of an aqueous solution of potassium hydroxide (85% potassium hydroxide 6.94 g (105.13 mmol)/water 40 ml). Then, the mixture was stirred at room temperature for 16 hours and the pH was adjusted to 7 by adding acetic acid.

The solvent was evaporated under reduced pressure. The residue was purified by column chromatography on silica gel eluting with ethyl acetate/methanol (=9/1) to give the desired ethyl 6-ethyl-4-hydroxypyrimidine-5-carboxylate (6.00 g, 64%).

mp: 84.5°–86° C., NMR (δ ppm, TMS/CDCl$_3$): 1.27 (3H,t,J=7), 1.38 (3H,t, J=7), 2.62 (2H,q,J=7), 4.41 (2H,q,J=7), 8.18 (1H,s).

EXAMPLE 2

According to the same manner as that described in Example 1, the compounds (Nos. IV-1 to IV-4 and IV-6) were synthesized. The physical properties of the compounds thus obtained are shown in Table 35.

TABLE 35

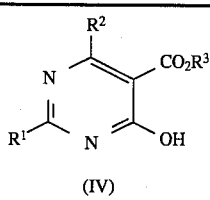

(IV)

| No | R$^1$ | R$^2$ | R$^3$ | mp | $^1$H-NMR (CDCl$_3$) δ ppm |
|---|---|---|---|---|---|
| IV-1 | H | CH$_3$ | CH$_3$ | 124–127° C. | 2.43 (3H, s), 3.94(3H, s), 8.16(1H, s). |
| IV-2 | H | CH$_3$ | C$_2$H$_5$ | oil | 1.39(3H, t, J=7), 2.42(3H, s), 4.40(2H, q, J=7), 8.18(1H, s), |
| IV-3 | CH$_3$ | CH$_3$ | C$_2$H$_5$ | 165–166° C. | 1.38(3H, t, J=7), 2.39(3H, s), 2.46(3H, s), 4.38(2H, q, J=7). |
| IV-4 | H | C$_2$H$_5$ | CH$_3$ | 107–110° C. | 1.26(3H, t, J=7), 2.64(2H, q, J=7), 3.99(3H, s), 8.18(1H, s). |
| IV-5 | H | C$_2$H$_5$ | C$_2$H$_5$ | 84.5–86° C. | 1.27(3H, t, J=7), 1.38(3H, t, J=7), 2.62(2H, q, J=7), 4.41 (2H, q, J=7) 8.18(1H, s). |
| IV-6 | CH$_3$ | C$_2$H$_5$ | C$_2$H$_5$ | 157–158° C. | 1.25(3H, t, J=7), 1.37(3H, t, J=7), 2.47(3H, s), 2.60(2H, q, J=7), 4.39(2H, q, J=7). |

EXAMPLE 3

Synthesis of Ethyl 4-Chloro-6-ethylpyrimidine-5-carboxylate (Compound No. II'-5)

Ethyl 6-ethyl-4-hydroxypyrimidine-5-carboxylate (7.30 g, 37.21 mmol) was stirred under ice-cooling. Phosphorus oxychloride (11.41 g, 74.41 mmol) was added dropwise to it. After the addition, the mixture was stirred at 90° C. for 3 hours. After cooling to room temperature, the mixture was poured into ice-cooled water and adjusted to pH 10 with an aqueous solution of sodium hydroxide. The resulting mixture was extracted with methylene chloride and dried over magnesium sulfate, and the solvent was evaporated. The residue was purified by column chromatography on silica gel eluting with n-hexane/ethyl acetate (=8/2) to give the desired ethyl 4-chloro-6-ethylpyrimidine-5-carboxylate (3.50 g, 44%).

NMR (δ ppm, TMS/CDCl$_3$): 1.31 (3H,t,J=7), 1.42 (3H, t,J=7), 2.81 (2H,q,J=7), 4.44 (2H,q,J=7), 8.92 (1H,s).

EXAMPLE 4

According to the same manner as that described in Example 3, the compounds (Nos. II'-1 to II'-4 and II'-6) were synthesized. The physical properties of the compounds thus obtained are shown in Table 36.

TABLE 36

| No | R$^1$ | R$^2$ | R$^3$ | mp | $^1$H-NMR (CDCl$_3$) δ ppm |
|---|---|---|---|---|---|
| II'-1 | H | CH$_3$ | CH$_3$ | oil | 2.56(3H, s), 4.00(3H, s), 8.89(1H, s). |
| II'-2 | H | CH$_3$ | C$_2$H$_5$ | oil | 1.43(3H, t, J=7), 2.57(3H, s), 4.47(2H, q, J=7), 8.88(1H, s). |
| II'-3 | CH$_3$ | CH$_3$ | C$_2$H$_5$ | oil | 1.41(3H, t, J=7), 2.52(3H, s), 2.69(3H, s), 4.44(2H, q, J=7). |
| II'-4 | H | C$_2$H$_5$ | CH$_3$ | oil | 1.31(3H, t, J=7), 2.79(2H, q, J=7), 3.99(3H, s), 8.93(1H, s). |
| II'-5 | H | C$_2$H$_5$ | C$_2$H$_5$ | oil | 1.31(3H, t, J=7), 1.42(3H, t, J=7), 2.81(2H, q, J=7), 4.44(2H, q, J=7), 8.92(1H, s). |
| II'-6 | CH$_3$ | C$_2$H$_5$ | C$_2$H$_5$ | oil | 1.29(3H, t, J=7), 1.41(3H, t, J=7), 2.70(3H, s), 2.76(2H, q, J=7), 4.45(2H, q, J=7). |

EXAMPLE 5

Synthesis of Ethyl 4-(2-(4-Butoxyphenyl)ethylamino)-6-ethylpyrimidine-5-carboxylate (Compound No. 3)

Triethylamine (1.89 g, 18.68 mmol) was added to a solution of ethyl 4-chloro-6-ethylpyrimidine-5-carboxylate (2.00 g, 9.32 mmol) in toluene (50 ml). The mixture was stirred at room temperature. Then, 4-butoxyphenethylamine (2.16 g, 11.18 mmol) was added. After stirring for 18 hours, water (40 ml) was added to the reaction mixture. The mixture was extracted with ethyl acetate and dried over magnesium sulfate. After evaporation of the solvent, the residue was purified by column chromatography on silica gel eluting with n-hexane/ethyl acetate (=8/2) to give the desired ethyl 4-(2-( 4-butoxyphenyl)ethylamino)-6-ethylpyrimidine-5-carboxylate (2.00 g, 58%).

NMR (δ ppm, TMS/CDCl$_3$): 0.94 (3H,t,J=7), 1.26 (3H, t,J=7), 1.37 (3H,t,J=7), 1.49 (2H,m), 1.74 (2H,m), 2.85 (2H,t,J=7), 2.90 (2H,q,J=7), 3.71 (2H,q,J=7), 3.91 (2H,t,J=6), 4.34 (2H,q,J=7), 6.83 (2H,d,J=9), 7.14 (2H,d,J=9), 8.01 (1H,brt), 8.51 (1H,s).

EXAMPLE 6

Synthesis of Ethyl 4-(1-(4-Butoxyphenyl)-1-propylamino)-6-ethylpyrimidine-5-carboxylate (Compound No. 6)

Triethylamine (0.33 g, 3.26 mmol) was added to a solution of ethyl 4-chloro-6-ethylpyrimidine-5-carboxylate (0.40 g, 1.86 mmol) in toluene (10 ml). The mixture was stirred at room temperature. Then, 1-(4-butoxyphenyl)-1-propylamine (0.46 g, 2.22 mmol) was added. After stirring at 80° C. for 3 hours, water (40 ml) was added to the reaction mixture. The mixture was extracted with methylene chloride and dried over magnesium sulfate. After evaporation of the solvent, the residue was purified by column chromatography on silica gel eluting with n-hexane/ethyl acetate (=8/2) to give The desired ethyl 4-(1-(4-butoxyphenyl)-1-propylamino)-6 -ethylpyrimidine-5-carboxylate (0.32 g, 44%).

NMR ($\delta$ ppm, TMS/CDCl$_3$): 0.91 (3H,t,J=7), 0.95 (3H,t, J=7), 1.25 (3H,t,J=7), 1.41 (3H,t,J=7) 1.47 (2H,m), 1.73 (2H,m), 1.87 (2H,m), 2.92 (2H,q,J=7), 3.93 (2H,t,J=7), 4.38 (2H,t,J=7), 5.16 (1H,q,J=7), 6.84 (2H,d,J=8), 7.24 (2H,d,J= 8), 8.45 (1 H,s), 8.50 (1 H,d,J=7).

EXAMPLE 7

Synthesis of Ethyl 4-(2-(4-Butylthiophenyl)ethylamino)-6-ethylpyrimidine-5-carboxylate (Compound No. 37)

Triethylamine (0.19 g, 1.88 mmol) was added to a solution of ethyl 4-chloro-6-ethylpyrimidine-5-carboxylate (0.20 g, 0.93 mmol) in toluene (4 ml). The mixture was stirred at room temperature. Then, 4-butylthiophenethylamine (0.20 g, 0.96 mmol) was added. After stirring for 3 hours, water (20 ml) was added to the reaction mixture. The mixture was extracted with methylene chloride and dried over magnesium sulfate. After evaporation of the solvent, the residue was purified by column chromatography on silica gel eluting with n-hexane/ethyl acetate (=8/2 ) to give the desired ethyl 4-(2 -(4 -butylthiophenyl)ethylamino)-6-ethylpyrimidine-5-carboxylate (0.20 g, 55%).

NMR ($\delta$ ppm, TMS/CDCl$_3$): 0.91 (3H,t,J=7), 1.26 (3H,t, J=7), 1.34 (3H,t,J=7), 1.46 (2H,m), 1.72 (2H,m), 2.91 (6H, m), 3.74 (2H, q, J=7 ), 4.34 (2H, q, J=7 ), 7.14 (2H, d, J=8), 7.27 (2H,d,J=8), 8.04 (1H,brt), 8.51 (1H,s).

EXAMPLE 8

Synthesis of Ethyl 4-(2-(4-Butylaminophenyl)ethylamino)- 6-ethyl pyrimidine-5-carboxylate (Compound No. 36)

Triethylamine (0.28 g, 2.77 mmol) was added to a solution of ethyl 4-chloro-6-ethylpyrimidine-5-carboxylate (0.30 g, 1.40 mmol) in toluene (10 ml). The mixture was stirred at room temperature. Then, 4-butylaminophenethylamine (0.40 g 2.08 mmol) was added after stirring for 3 hours, water (20 ml) was added to the reaction mixture. The mixture was extracted with methylene chloride and dried over magnesium sulfate. After evaporation of the solvent, the residue was purified by column chromatography on silica gel eluting with n-hexane/ethyl acetate (=8/2) to give the desired ethyl 4-(2 -(4-butylaminophenyl)ethylamino)-6-ethylpyrimidine-5-carboxylate (0.30 g, 58%).

mp: 65°–66° C., NMR ($\delta$ ppm, TMS/CDCl$_3$): 0.95 (3H, t,J=7), 1.25 (3H,t, J=7), 1.36 (3H,t,J=7), 1.45 (2H,m), 1.70 (2H,m), 2.80 (2H,t,J=7), 2.89 (2H,q,J=7), 3.09 (2H,t,J=7), 3.69 (2H,q,J=7), 4.84 (2H,q, J=7), 6.55 (2H, d, J=9 ), 7.04 (2H,d,J=9), 7.98 (1H,brt), 8.51 (1H,s).

EXAMPLE 9

Synthesis of Ethyl 4-(2-(4-(2-(Tetrahydropyran-2-yloxy)ethyl)phenyl)ethylamino)- 6-ethylpyrimidine-5-carboxylate (Compound No. 51)

Triethylamine (2.26 g, 22.33 mmol) was added to a solution of ethyl 4-chloro-6-ethylpyrimidine-5-carboxylate (2.41 g, 11.23 mmol) in toluene (10 ml). The mixture was stirred at room temperature. Then, 4-(2-tetrahydropyran-2-yloxy)ethyl)phenethylamine (2.80 1 1.23 mmol) was added. After stirring for 16 hours, water (40 ml) was added to the reaction mixture. The mixture was extracted with methylene chloride and dried over magnesium sulfate. After evaporation of The solvent, the residue was purified by column chromatography on silica gel eluting with n-hexane/ethyl acetate (=8/2) to give the desired ethyl 4-(2-(4-(2-(tetrahydropyran- 2-yloxy)ethyl)phenyl)ethylamino)-6-ethylpyrimidine-5-carboxylate (4.20 g, 87%).

NMR ($\delta$ ppm, TMS/CDCl$_3$): 1.26 (3H,t,J=7), 1.37 (3H,t, J=7), 1.40–1.80 (6H,m), 2.90 (4H,m), 3.50–4.20 (8H,m), 4.34 (2H,q,J=7), 4.70 (1H,m), 6.87 (2H,d,J=9), 7.14 (2H,d, J=9), 8.02 (1H,brt), 8.51 (1H,s).

EXAMPLE 10

Synthesis of Ethyl 4-(2-(4-(2-Hydroxyethyl)phenyl)ethylamino)- 6-ethylpyrimidine-5-carboxylate (Compound No. 49)

p-Toluenesulfonic acid (0.10 g) was added to a solution of ethyl 4-(2-(4-(2-(tetrahydropyran-2-yloxy)ethyl)phenyl) ethylamino)- 6-ethylpyrimidine-S-carboxylate (4.20 g, 9.82 mmol) in ethanol (40 ml). The mixture was heated under reflux for 4 hours. After cooling to room temperature, the solvent was evaporated under reduced pressure. Water (40 ml) was added to the residue. The mixture was extracted with methylene chloride and dried over magnesium sulfate. After evaporation of the solvent, the residue was purified by column chromatography on silica gel eluting with n-hexane/ethyl acetate (=1/1) to give the desired ethyl 4-(2-(4-(2-hydroxyethyl)phenyl)ethylamino)- 6-ethylpyrimidine-5-carboxylate (2.60 g, 77%).

mp: 68°–71° C., NMR ($\delta$ ppm, TMS/CDCl$_3$): 1.26 (3H, t,J=7), 1.37 (3H,t, J=7), 2.90 (6H, m), 3.73 (2H, q, J=7 ), 3.85 (2H,t,J=7 ), 4.33 (2H,q,J=7), 7.18 (4H,s), 8.01 (1H,brt), 8.50 (1H,s).

EXAMPLE 11

Synthesis of Ethyl 4-(2-(4-(2-Methylsulfonyloxyethyl)phenyl)ethylamino)- 6-ethylpyrimidine-5-carboxylate (Compound No. 50)

Triethylamine (0.88 g, 8.70 mmol) was added to a solution of ethyl 4-(2-(4-(2-hydroxyethyl)phenyl)ethylamino)- 6-ethylpyrimidine-5-carboxylate (1.50 g, 4.37 mmol) in methylene chloride (40 ml). The mixture was stirred under ice-cooling, and methanesulfonyl chloride (0.60 g, 5.24 mmol) was added dropwise to the mixture. The resulting mixture was stirred under ice-cooling for 10 minutes after the addition. Then, water (40 ml) was added to the reaction mixture. The mixture was extracted with methylene chloride and dried over magnesium sulfate. After evaporation of the solvent, the residue was purified by column chromatography on silica gel eluting with n-hexane/ethyl acetate (=1/1) to give the desired ethyl 4-(2-(4-(2-methylsulfonyloxyethyl)phenyl)ethylamino)- 6-ethylpyrimidine-5-carboxylate (1.80 g, 98%).

mp: 84°–86° C., NMR ($\delta$ ppm, TMS/CDCl$_3$): 1.26 (3H, t,J=7 ), 1.38 (3H,t, J=7), 2.84 (3H,s), 2.93 (4H,q,J=7 ), 3.03 (2H, t, J=7), 3.74 (2H,q,J=7), 4.34 (2H,q,J=7), 4.40 (2H,t, J=7), 7.19 (4H,s), 8.06 (1H,brt), 8.52 (1H,s).

EXAMPLE 12

Synthesis of Ethyl 4-(2-(4-(2-ethylaminoethyl)phenyl)ethylamino)-6-ethylpyrimidine-5-carboxylate (Compound No. 55)

A 70% aqueous ethylamine solution (2.14 g, 33.23 mmol) was added to ethyl 4-(2-(4-(2-methylsulfonyloxyethyl)-phenyl)ethylamino)-6 -ethylpyrimidine-5-carboxylate (0.70 g, 1.66 mmol). The mixture was stirred at 100° C. for 2 hours in a sealed tube and cooled to room temperature. Then, water (40 ml) was added to the reaction mixture. The mixture was extracted with methylene chloride and dried over magnesium sulfate. After evaporation of the solvent, the residue was purified by column chromatography on silica gel eluting with ethyl acetate/methanol (=8/2) to give the desired ethyl 4-(2-( 4-(2-ethylaminoethyl)phenyl)ethylamino)-6-ethyl pyrimidine-5-carboxylate (0.40 g, 65%).

NMR ($\delta$ ppm, TMS/CDCl$_3$): 1.10 (3H,t,J=7), 1.26 (3H,t, J=7), 1.37 (3H,t,J=7 ), 2.67 (2H,q,J=7), 2.87 (8H,m), 3.74 (2H,t,J=7), 4.34 (2H,q,J=7), 7.16 (4H,s), 8.02 (l H,brt), 8.51 (1H,s).

EXAMPLE 13

Synthesis of Ethyl 4-(2-(4-(2-Methylthioethyl)phenyl)ethylamino)-6-ethylpyrimidine-5-carboxylate (Compound No. 72)

A solution of ethyl 4-(2-(4-(2-methylsulfonyloxyethyl)phenyl)ethylamino)- 6-ethylpyrimidine-5-carboxylate (0.70 g, 1.66 mmol) in N,N-dimethylformamide (10 ml) was stirred under ice-cooling. Sodium thiomethoxide (0.13 g, 1.85 mmol) was added to the solution. The mixture was stirred under ice-cooling for 2 hours, and then water (40 ml) was added. The mixture was extracted with ethyl ether and dried over magnesium sulfate. After evaporation of the solvent, the residue was purified by column chromatography on silica gel eluting with n-hexane/ethyl acetate (=8/2) to give the desired ethyl 4-(2-(4-(2-methylthioethyl)phenyl)ethylamino)-6 -ethylpyrimidine-5-carboxylate (0.47 g, 76%).

NMR ($\delta$ ppm, TMS/CDCl$_3$): 1.26 (3H,t,J=7), 1.37 (3H,t, J=7), 2.18 (3H,s), 2.73 (2H,m), 2.90 (6H,m), 3.74 (2H,q,J= 7), 4.34 (2H,q,J=7), 7.16 (4H,s), 8.03 (1H,brt), 8.51 (1H,s).

EXAMPLE 14

Synthesis of Ethyl 4-(2-(4-(2-Methylsulfinylethyl)phenyl)ethylamino)-6-ethylpyrimidine-5-carboxylate (Compound No. 73)

A solution of ethyl 4-(2-(4-(2-methylthioethyl)phenyl)ethylamino)- 6-ethylpyrimidine-5-carboxylate (0.25 g, 0.67 mmol) in methylene chloride (20 ml) was stirred under ice-cooling. 80% m-Chloroperbenzoic acid (0.16 g, 0.74 mmol) was added to the solution. The mixture was stirred under ice-cooling for 20 minutes, and then a 1N aqueous solution (20 ml) of sodium hydroxide was added. The mixture was extracted with methylene chloride and dried over magnesium sulfate. After evaporation of the solvent, the residue was purified by column chromatography on silica gel eluting with ethyl acetate/methanol (=8/2) to give the desired ethyl 4-(2-(4-(2-methylsulfinylethyl)phenyl) ethylamino)- 6-ethylpyrimidine-5-carboxylate (0.20 g, 77%).

NMR ($\delta$ ppm, TMS/CDCl$_3$): 1.26 (3H,t,J=7), 1.38 (3H,t, J=7), 2.58 (3H,s), 2.97 (6H,m), 3.07 (2H,m), 3.74 (2H,q,J= 7), 4.34 (2H,q,J=7), 7.16 (4H,s), 8.07 (1H,brt), 8.51 (1H,s).

EXAMPLE 15

Synthesis of 4-(2-(4-Butoxyphenyl)ethylamino)-6ethylpyrimidine-5-carboxylic Acid (Compound No. 74)

A solution of ethyl 4-(2-(4-butoxyphenyl)ethylamino)-6-ethyl pyrimidine-5-carboxylate (1.00 g, 2.69mmol) in ethanol (10 ml) was stirred at room temperature. An aqueous solution of sodium hydroxide (sodium hydroxide 0.53 g (13.24 mmol)/water 10 mi) was added to the solution. Then the mixture was stirred at room temperature for 4 hours and adjusted to pH 4 with 1N hydrochloric acid. The resulting mixture was extracted with methylene chloride and dried over magnesium sulfate, and the solvent was evaporated. The residue was recrystallized from methanol to give the desired 4-(2-(4-butoxyphenyl)ethylamino)-6-ethylpyrimidine-5 -carboxylic acid (0.83 g, 90%).

mp: 208°–211° C., NMR ($\delta$ ppm, TMS/CDCl$_3$): 0.95 (3H,t,J=7), 1.39 (3H,t, J=7), 1.41 (2H,m), 1.73 (2H,m), 2.91 (2H,t,J=7), 3.36 (2H,q,J=7), 3.82 (2H,q,J=7), 3.93 (2H,t,J= 7), 6.48 (2H,d,J=9), 7.16 (2H,d,J=9), 8.70 (1H,s), 11.01 (1H,brs).

EXAMPLE 16

Synthesis of Methyl 4-(2-(4-Butoxyphenyl)ethylamino)-6-ethylpyrimidine-5-carboxylate (Compound No. 2)

Potassium carbonate (0.27 g, 1.95 mmol) was added to a solution of 4-(2-(4-butoxyphenyl)ethylamino)-6-ethylpyrimidine- 5-carboxylic acid (0.34 g, 0.99 mmol) in ethyl methyl ketone (20 ml), and methyl iodide (0.42 g, 2.96 mmol) was added. After stirring at 65° C. for 3 hours, the mixture was cooled to room temperature. The resulting solid was filtered off and the solvent was evaporated. The residue was purified by column chromatography on silica gel eluting with n-hexane/ethyl acetate (=8/2) to give the desired methyl 4-( 2-(4-butoxyphenyl)ethylamino)-6-ethylpyrimidine-5-carboxylate (0.26 g, 73%).

NMR (δ ppm, TMS/CDCl₃): 0.94 (3H,t,J=7), 1.25 (3H, t,J=7), 1.49 (2H,m), 1.76 (2H,m), 2.86 (2H,t,J=7), 2.92 (2H, q, J=7), 3.73 (2H, q, J=7), 3.86 (3H, s), 3.94 (2H,t,J=7), 6.84 (2H,d,J=9), 7.13 (2H,d,J=9), 7.96 (1H,brt), 8.52 (1H,s).

EXAMPLE 17

Synthesis of Ethyl 4-(2-(3,4-Dimethoxyphenyl)ethylamino)-6-ethyl-2-methylthiopyrimidine-5-carboxylate (Compound No. 67)

Triethylamine (0.17 g, 1.68 mmol) was added to a solution of ethyl 4-chloro-5-ethyl-2-methylthiopyrimidine-5-carboxylate (0.21 g, 0.81 mmol) in toluene (4 ml), followed by addition of 3,4-dimethoxyphenethylamine (0.18 g, 0.99 mmol). The mixture was stirred at room temperature for 14 hours. The reaction mixture was poured into water, extracted with ethyl acetate and dried over magnesium sulfate. After evaporation of the solvent, the residue was purified by column chromatography on silica gel eluting with n-hexane/ethyl acetate (=8/2 ) to give the desired ethyl 4-(2-(3,4-dimethoxyphenyl)ethylamino)- 6-ethyl-2-methylthiopyrimidine-5-carboxylate (0.16 g, 49%).

mp: 52°–53° C., NMR (δ ppm, TMS/CDCl₃): 1.22 (3H, t,J=7), 1.35 (3H,t,J=7), 2.54 (3H, s), 2.86 (2H,t,J=7), 2.89 (2H,q,J=7), 3.74 (2H,q,J=7), 3.87 (3H,s), 3.88 (3H,s), 4.30 (2H,q,J=7), 6.74 (1H,s), 6.77 (2H,m)), 8.37 (1H,brt).

EXAMPLE 18

According to the same manner as that described in Examples 5 to 17, Compound Nos. 1, 4, 5, 7 to 35, 38 to 48, 52 to 54, 56 to 66, 68 to 71 and 75 to 327 were synthesized.

The physical properties of the compounds thus obtained are shown in Tables 37 to 59.

TABLE 37

| No | mp | ¹H-NMR (CDCl₃) δ ppm |
|---|---|---|
| 1 | 36.5–38° C. | 1.26(3H, t, J=7), 1.30(9H, s), 1.35(3H, t, J=7), 2.89(2H, t, J=7) 2.93(2H, q, J=7), 3.75(2H, q, J=7), 4.33(2H, q, J=7), 7.14(2H, d, J=9), 7.33(2H, d, J=9), 7.98(1H, brt), 8.51(1H, s). |
| 2 | oil | 0.94(3H, t, J=7), 1.25(3H, t, J=7), 1.49(2H, m), 1.76(2H, m), 2.86(2H, t, J=7), 2.92(2H, q, J=7), 3.73(2H, q, J=7), 3.86(3H, s), 3.94(2H, t, J=7), 6.84(2H, d, J=9), 7.13(2H, d, J=9), 7.96(1H, brt), 8.52(1H, s). |
| 3 | oil | 0.96(3H, t, J=7), 1.26(3H, t, J=7), 1.37(3H, t, J=7), 1.49(2H, m), 1.74(2H, m), 2.85(2H, t, J=7), 2.90(2H, q, J=7), 3.71(2H, q, J=7), 3.91(2H, t, J=6), 4.34(2H, q, J=7), 6.83(2H, d, J=9), 7.14(2H, d, J=9), 8.01(1H, brt), 8.51(1H, s). |
| 4 | 32–33° C. | 0.97(3H, t, J=7), 1.26(3H, t, J=7), 1.36(3H, t, J=7), 1.49(2H, m), 1.74(2H, m), 2.64(2H, q, J=7), 2.85(2H, t, J=7), 2.92(3H, s), 3.76(2H, t, J=7), 3.93(2H, t, J=7), 4.33(2H, q, J=7), 6.82(2H, d, J=8), 7.13(2H, d, J=8), 8.53(1H, s). |
| 5 | oil | 0.96(3H, t, J=7), 1.26(3H, t, J=7), 1.40(3H, t, J=7), 1.47(2H, m), 1.54(3H, d, J=7), 1.74(2H, m), 2.93(2H, q, J=7), 3.93(2H, t, J=7), 4.36(2H, q, J=7), 5.36(1H, m), 6.85(2H, d, J=9), 7.27(2H, d, J=9), 8.41(1H, d, J=7), 8.48(1H, s). |

TABLE 38

| No | mp | ¹H-NMR (CDCl₃) δ ppm |
|---|---|---|
| 6 | oil | 0.91(3H, t, J), 0.95(3H, t, J=7), 1.25(3H, t, J=7), 1.41(3H, t, J=7), 1.47(2H, m), 1.73(2H, m), 1.87(2H, m), 2.92(2H, q, J=7), 3.93(2H, t, J=7), 4.38(2H, t, J=7), 5.16(1H, q, J=7), 6.84(2H, d, J=8), 7.24(2H, d, J=8), 8.45(1H, s), 8.50(1H, d, J=7). |
| 7 | oil | 0.96(3H, t, J=7), 1.27(3H, t, J=7), 1.35(3H, t, J=7), 1.47(2H, m), 1.75(2H, m), 2.95(2H, q, J=7), 3.94(2H, t, J=7), 4.35(2H, q, J=7), 4.64(2H, d, J=6), 6.86(2H, d, J=9), 7.25(2H, d, J=9), 8.28(1H, t, J=6), 8.53(1H, s). |
| 8 | oil | 0.97(3H, t, J=7), 1.37(3H, t, J=7), 1.49(2H, m), 1.76(2H, m), 2.62(3H, s), 2.86(2H, t, J=7), 3.73(2H, q, J=7), 3.93(2H, t, J=7), 4.34(2H, q, J=7), 6.84(2H, d, J=9), 7.14(2H, d, J=9), 8.23(1H, brt), 8.47(1H, s). |
| 9 | 93.5–94° C. | 1.31(9H, s), 1.33(3H, t, J=7), 1.37(3H, t, J=7), 2.97(2H, t, J=7), 3.04(2H, q, J=7), 3.89(2H, q, J=7), 4.34(2H, q, J=7), 7.22(2H, d, J=9), 7.34(2H, d, J=9), 7.47(3H, dd, J=7, 4), 8.13(1H, brt), 8.50(2H, dd, J=7, 4). |

TABLE 39

| No | mp | ¹H-NMR (CDCl₃) δ ppm |
|---|---|---|
| 10 | oil | 0.97(3H, t, J=7), 1.24(3H, t, J=7), 1.36(3H, t, J=7), 1.48(2H, m), |

TABLE 39-continued

| No | mp | $^1$H-NMR (CDCl$_3$) δ ppm |
|---|---|---|
| | | 1.76(2H, m), 2.50(3H, s), 2.84(2H, t, J=7), 2.89(2H, q, J=7), 3.72(2H, q, J=7), 3.94(2H, q, J=7), 4.32(2H, q, J=7), 6.84(2H, d, J=9), 7.14(2H, d, J=9), 8.05(1H, brt). |
| 11 | 61~62° C. | 1.25(3H, t, J=7), 1.31(9H, s), 2.89(2H, t, J=7), 2.92(2H, q, J=7), 3.75(2H, q, J=7), 3.86(3H, s), 7.17(2H, d, J=8), 7.33(2H, d, J=8), 7.98(1H, brt), 8.52(1H, s). |
| 12 | oil | 0.97(3H, t, J=7), 1.01(3H, t, J=7), 1.26(3H, t, J=7), 1.46(2H, m), 1.74(4H, m), 2.87(2H, t, J=7), 2.93(2H, q, J=7), 3.72(2H, q, J=7), 3.93(2H, t, J=7), 4.23(2H, q, J=7), 6.84(2H, d, J=9), 7.14(2H, d, J=9), 8.01(1H, brt), 8.52(1H, s). |
| 13 | oil | 0.97(3H, t, J=7), 1.26(3H, t, J=7), 1.35(6H, d, J=6), 1.46(2H, m), 1.76(2H, m), 2.86(2H, t, J=7), 2.91(2H, q, J=7), 3.71(2H, q, J=7), 3.93(2H, t, J=7), 5.22(1H, m), 6.83(2H, d, J=9), 7.14(2H, d, J=9), 8.01(1H, brt), 8.51(1H, s). |
| 14 | oil | 0.97(3H, t, J=7), 1.25(3H, t, J=7), 1.33(3H, t, J=7), 1.48(4H, m), 1.74(4H, m), 2.87(2H, t, J=7), 2.93(2H, q, J=7), 3.71(2H, q, J=7), 3.93(2H, t, J=7), 4.27(2H, t, J=7), 6.83(2H, d, J=9), 7.14(2H, d, J=9), 8.02(1H, brt), 8.52(1H, s). |

TABLE 40

| No | mp | $^1$H-NMR (CDCl$_3$) δ ppm |
|---|---|---|
| 15 | oil | 0.97(3H, t, J=7), 1.15(3H, t, J=7), 1.47(2H, m), 1.76(2H, m), 2.84(2H, t, J=7), 2.86(2H, q, J=7), 3.70(2Hq, J=7), 3.93(2H, t, J=7), 5.30(2H, s), 6.83(2H, d, J=9), 7.12(2H, d, J=9), 7.38(5H, s), 7.98(1H, brt), 8.51(1H, s). |
| 16 | oil | 0.97(3H, t, J=7), 1.26(3H, t, J=7), 1.31(9H, s), 1.45(2H, m), 1.69(2H, m), 2.88(2H, t, J=7), 2.93(2H, q, J=7), 3.74(2H, q, J=7), 4.28(2H, q, J=7), 7.18(2H, d, J=8), 7.33(2H, d, J=8), 8.05(1H, brt), 8.52(1H, s). |
| 17 | 38~39° C. | 1.26(3H, t, J=7), 1.36(3H, t, J=7), 1.40(3H, t, J=7), 2.86(2H, t, J=7), 2.92(2H, q, J=7), 3.72(2H, q, J=7), 4.01(2H, q, J=7), 4.34(2H, q, J=7), 6.83(2H, d, J=9), 7.14(2H, d, J=9), 8.01(1H, brt), 8.51(1H, s). |
| 18 | 60~61° C. | 1.02(3H, t, J=7), 1.26(3H, t, J=7), 1.36(3H, t, J=7), 1.74(2H, m), 2.86(2H, t, J=7), 2.92(2H, q, J=7), 3.72(2H, t, J=7), 3.90(2H, t, J=7), 4.34(2H, q, J=7), 6.84(2H, d, J=9), 7.14(2H, d, J=9), 8.02(1H, brt), 8.52(1H, s). |

TABLE 41

| No | mp | $^1$H-NMR (CDCl$_3$) δ ppm |
|---|---|---|
| 19 | oil | 0.90(3H, t, J=7), 1.26(3H, t, J=7), 1.20~1.40(9H. m), 1.74(2H, m), 2.86(2H, t, J=7), 2.92(2H, q, J=7), 3.72(2H, q, J=7), 3.93(2H, t, J=7), 4.34(2H, q, J=7), 6.84(2H, d, J=9), 7.14(2H, d, J=9), 8.01(1H, brt), 8.52(1H, s). |
| 20 | oil | 1.20(3H, t, J=7), 1.26(3H, t, J=7), 1.36(3H, t, J=7), 2.87(4H, t, J=7), 2.91(2H, q, J=7), 3.50(2H, q, J=7), 3.61(2H, t, J=7), 3.73(2H, q, J=7), 4.33(2H, q, J=7), 7.16(4H, s), 8.02(1H, brt), 8.52(1H, s). |
| 21 | oil | 1.01(3H, t, J=7), 1.20(3H, t, J=7), 1.26(3H, t, J=7), 1.73(2H, m), 2.87(4H, t, J=7), 2.93(2H, q, J=7), 3.50(2H, q, J=7), 3.61(2H, t, J=7), 3.73(2H, q, J=7), 4.24(2H, t, J=7), 7.16(4H, s), 8.04(1H, brt), 8.52(1H, s). |
| 22 | oil | 1.20(3H, t, J=7), 1.26(3H, t, J=7), 1.34(6H, d, J=7), 2.86(4H, t, J=7), 2.91(2H, q, J=7), 3.50(2H, q, J=7), 3.61(2H, t, J=7), 3.73(2H, q, J=7), 5.22(1H, m), 7.16(4H, s), 8.01(1H, brt), 8.51(1H, s). |
| 23 | 73~74° C. | 1.26(3H, t, J=7), 1.38(3H, t, J=7), 2.33(3H, s), 2.89(2H, t, J=7), 2.93(2H, q, J=7), 3.70(2H, q, J=7), 4.34(2H, q, J=7), 7.10~7.15(3H, m), 8.09(1H, brt), 8.52(1H, s). |

TABLE 42

| No | mp | $^1$H-NMR (CDCl$_3$) δ ppm |
|---|---|---|
| 24 | 42–44° C. | 0.97(3H, t, J=7), 1.26(3H, t, J=7), 1.36(3H, t, J=7), 1.47(2H, m), 1.76(2H, m), 2.20(3H, s), 2.82(2H, t, J=7), 2.92(2H, q, J=7), 3.70(2H, q, J=7), 3.94(2H, t, J=7), 4.34(2H, q, J=7), 6.74(1H, d, J=9), 6.99(1H, d, J=9), 7.01(1H, s), 8.00(1H, brt), 8.52(1H, s). |
| 25 | 49–51° C. | 0.98(3H, t, J=7), 1.26(3H, t, J=7), 1.37(3H, t, J=7), 1.45(2H, m), 1.80(2H, m), 2.83(2H, t, J=7), 2.93(2H, q, J=7), 3.71(2H, q, J=7), 4.00(2H, t, J=7), 4.34(2H, q, J=7), 6.85(1H, d, J=9), 7.05(1H, dd, J=9,2), 7.23(1H, d, J=2), 8.02(1H, brt), 8.52(1H, s). |
| 26 | 40–40.5° C. | 1.26(3H, t, J=7), 1.36(3H, t, J=7), 2.23(3H, s), 2.24(3H, s), 2.85(2H, t, J=7), 2.92(2H, q, J=7), 3.72(2H, q, J=7), 4.33(2H, q, J=7), 6.97(1H, d, J=8), 7.01(1H, s), 7.07(1H, d, J=8), 8.01(1H, brt), 8.51(1H, s). |
| 27 | 58–60° C. | 1.26(3H, t, J=7), 1.38(3H, t, J=7), 2.29(3H, s), 2.33(3H, s), 2.89(2H, t, J=7), 2.92(2H, q, J=7), 3.69(2H, q, J=7), 4.35(2H, q, J=7), 7.00(3H, m), 8.02(1H, brt), 8.52(1H, s). |

TABLE 43

| No | mp | $^1$H-NMR (CDCl$_3$) δ ppm |
|---|---|---|
| 28 | 59.5–60° C. | 1.26(3H, t, J=7), 1.38(3H, t, J=7), 2.88(2H, t, J=7), 2.92(2H, q, J=7), 3.70(2H, q, J=7), 4.36(2H, q, J=7), 7.07(1H, dd, J=9,2), 7.31(1H, d, J=2), 7.37(1H, d, J=9), 8.08(1H, brt), 8.52(1H, s). |
| 29 | 84–85° C. | 1.27(3H, t, J=7), 1.39(3H, t, J=7), 2.93(2H, q, J=7), 3.03(2H, t, J=7), 3.78(2H, q, J=7), 4.35(2H, q, J=7), 7.17(2H, s), 7.38(1H, s), 8.07(1H, brt), 8.53(1H, s). |
| 30 | 70–72° C. | 1.26(3H, t, J=7), 1.36(3H, t, J=7), 2.93(2H, q, J=7), 3.27(2H, q, J=7), 3.80(2H, q, J=7), 4.36(2H, q, J=7), 7.09(1H, d, J=8), 7.28(2H, d, J=8), 8.04(1H, brt), 8.49(1H, s). |
| 31 | oil | 1.26(3H, t, J=7), 1.37(3H, t, J=7), 2.92(2H, q, J=7), 2.98(2H, t, J=7), 3.78(2H, q, J=7), 4.34(2H, q, J=7), 7.43(4H, m), 8.10(1H, brt), 8.52(1H, s). |
| 32 | oil | 0.97(3H, t, J=7), 1.25(3H, t, J=7), 1.36(3H, t, J=7), 1.49(2H, m), 1.78(2H, m), 2.89(2H, t, J=7), 2.92(2H, q, J=7), 3.74(2H, q, J=7), 3.96(2H, t, J=7), 4.34(2H, q, J=7), 6.86(1H, d, J=8), 6.87(1H, t, J=8), 7.19(1H, d, J=8), 7.20(1H, t, J=8), 7.94(1H, brt), 8.50(1H, s). |

TABLE 44

| No | mp | $^1$H-NMR (CDCl$_3$) δ ppm |
|---|---|---|
| 33 | oil | 0.97(3H, t, J=7), 1.26(2H, t, J=7), 1.37(3H, t, J=7), 1.49(2H, m), 1.78(2H, m), 2.89(2H, t, J=7), 2.92(2H, q, J=7), 3.74(2H, q, J=7), 3.95(2H, t, J=7), 4.34(2H, q, J=7), 6.78(3H, m), 7.21(1H, t, J=8), 8.01(1H, brt), 8.51(1H, s). |
| 34 | 47–48° C. | 1.26(3H, t, J=7), 1.29(9H, s), 1.39(3H, t, J=7), 2.94(2H, q, J=7), 3.92(2H, q, J=6), 4.14(2H, t, J=6), 4.35(2H, q, J=7), 6.87(2H, d, J=9), 7.31(2H, d, J=9), 8.33(1H, brt), 8.51(1H, s). |
| 35 | 42–43° C. | 0.93(3H, t, J=7), 1.26(3H, t, J=7), 1.39(3H, t, J=7), 1.46(2H, m), 1.76(2H, m), 2.94(2H, q, J=7), 3.88(2H, q, J=7), 3.90(2H, t, J=6), 4.10(2H, t, J=6), 4.34(2H, q, J=7), 6.86(4H, m), 8.32(1H, brt), 8.51(1H, s). |
| 36 | 65–66° C. | 0.95(3H, t, J=7), 1.25(3H, t, J=7), 1.36(3H, t, J=7), 1.45(2H, m), 1.70(2H, m), 2.80(2H, t, J=7), 2.89(2H, q, J=7), 3.09(2H, t, J=7), 3.69(2H, q, J=7), 4.34(2H, q, J=7), 6.55(2H, d, J=9), 7.04(2H, d, J=9), 7.98(1H, brt), 8.51(1H, s). |

TABLE 45

| No | mp | $^1$H-NMR (CDCl$_3$) δ ppm |
|---|---|---|
| 37 | oil | 0.91(3H, t, J=7), 1.26(3H, t, J=7), 1.34(3H, t, J=7), 1.46(2H, m), 1.72(2H, m), 2.91(6H, m), 3.74(2H, q, J=7), 4.34(2H, q, J=7), |

TABLE 45-continued

| No | mp | ¹H-NMR (CDCl₃) δ ppm |
|---|---|---|
| 38 | 110~111° C. | 7.14(2H, d, J=8), 7.27(2H, d, J=8), 8.04(1H, brt), 8.51(1H, s).<br>1.27(3H, t, J=7), 1.39(3H, t, J=7), 2.94(2H, q, J=7), 3.05(2H, t, J=7),<br>3.78(2H, q, J=7), 4.34(2H, q, J=7), 7.39(2H, t, J=9), 8.18(2H, d, J=9),<br>8.17(1H, brt), 8.53(1H, s). |
| 39 | oil | 1.26(3H, t, J=7), 1.37(3H, t, J=7), 2.89(2H, t, J=7), 2.92(2H, q, J=7),<br>3.73(2H, q, J=7), 4.34(2H, q, J=7), 6.99(2H, t, J=9),<br>7.20(2H, dd, J=9,6), 8.05(1H, brt), 8.51(1H, s). |
| 40 | 52.5~<br>53.5° C. | 1.26(3H, t, J=7), 1.37(3H, t, J=7), 2.21(3H, s), 2.90(6H, m),<br>3.72(2H, q, J=7), 4.14(2H, q, J=7), 4.34(2H, q, J=7), 6.85(2H, d, J=9),<br>7.14(2H, d, J=9), 8.04(1H, brt), 8.52(1H, s). |
| 41 | 83~84° C. | 1.26(3H, t, J=7), 1.37(3H, t, J=7), 2.70(3H, s), 2.87(2H, t, J=7),<br>2.92(2H, q, J=7), 3.14(2H, m), 3.74(2H, q, J=7), 4.34(2H, q, J=7),<br>4.41(2H, t, J=7), 6.86(2H, d, J=9), 7.16(2H, d, J=9), 8.05(1H, brt),<br>8.52(1H, s). |

TABLE 46

| No | mp | ¹H-NMR (CDCl₃) δ ppm |
|---|---|---|
| 42 | 38.5~<br>40° C. | 1.24(3H, t, J=7), 1.26(3H, t, J=7), 1.37(3H, t, J=7), 2.86(2H, t, J=7),<br>2.92(2H, q, J=7), 3.60(2H, q, J=7), 3.72(2H, q, J=7), 3.78(2H, t, J=5),<br>4.10(2H, t, J=5), 4.34(2H, q, J=7), 6.87(2H, d, J=9), 7.14(2H, d, J=9),<br>8.02(1H, brt), 8.52(1H, s). |
| 43 | 49~50° C. | 1.16(3H, t, J=7), 1.26(3H, t, J=7), 1.37(3H, t, J=7), 2.74(2H, q, J=7),<br>2.86(2H, t, J=7), 2.89(2H, q, J=7), 3.02(2H, t, J=5), 3.73(2H, q, J=7),<br>4.07(2H, t, J=5), 4.34(2H, q, J=7), 6.86(2H, d, J=9), 7.14(2H, d, J=9),<br>8.02(1H, brt), 8.51(1H, s). |
| 44 | oil | 1.06(6H, t, J=7), 1.26(3H, t, J=7), 1.37(3H, t, J=7), 2.64(4H, q, J=7),<br>2.92(6H, m), 3.71(2H, q, J=7), 4.04(2H, t, J=7), 4.34(2H, q, J=7),<br>6.85(2H, d, J=9), 7.13(2H, d, J=9), 8.02(1H, brt), 8.51(1H, s). |
| 45 | 58~59° C. | 1.26(3H, t, J=7), 1.37(3H, t, J=7), 2.89(2H, t, J=7), 2.92(2H, q, J=7),<br>3.74(2H, q, J=7), 4.34(2H, q, J=7), 7.15(2H, d, J=9), 7.25(2H, d, J=9),<br>8.06(1H, brt), 8.51(1H, s). |

TABLE 47

| No | mp | ¹H-NMR (CDCl₃) δ ppm |
|---|---|---|
| 46 | 34~35° C. | 1.26(3H, t, J=7), 1.36(3H, t, J=7), 2.32(3H, s), 2.88(2H, t, J=7),<br>2.92(2H, q, J=7), 3.74(2H, q, J=7), 4.30(2H, q, J=7), 7.12(4H, s),<br>8.02(1H, brt), 8.52(1H, s). |
| 47 | oil | 0.92(3H, t, J=7), 1.26(3H, t, J=7), 1.36(3H, t, J=7), 1.56(4H, m),<br>2.58(2H, t, J=7), 2.88(2H, t, J=7), 2.91(2H, q, J=7), 3.74(2H, q, J=7),<br>4.34(2H, q, J=7), 7.13(4H, s), 8.00(1H, brt), 8.51(1H, s). |
| 48 | 40.5~<br>41.5° C. | 1.14(6H, t, J=7), 1.26(3H,t, J=7), 1.36(3H, t, J=7), 2.81(2H, t, J=7),<br>2.91(2H, q, J=7), 3.30(4H, q, J=7), 3.70(2H, q, J=7), 4.34(2H, q, J=7),<br>6.64(2H, d, J=9), 7.09(2H,d, J=9), 7.98(1H, brt), 8.51(1H, s). |
| 49 | 68~71° C. | 1.26(3H, t, J=7), 1.37(3H, t, J=7), 2.90(6H, m), 3.73(2H, q, J=7),<br>3.85(2H, t, J=7), 4.33(2H, q, J=7), 7.18(4H, s), 8.01(1H, brt),<br>8.50(1H, s). |
| 50 | 84~86° C. | 1.26(3H, t, J=7), 1.38(3H, t, J=7), 2.84(3H, s), 2.93(4H, q, J=7),<br>3.03(2H, t, J=7), 3.74(2H, q, J=7), 4.34(2H, q, J=7), 4.40(2H, t, J=7),<br>7.19(4H, s), 8.06(1H, brt), 8.52(1H, s). |

TABLE 48

| No | mp | ¹H-NMR (CDCl₃) δ ppm |
|---|---|---|
| 51 | oil | 1.26(3H, t, J=7), 1.38(3H, t, J=7), 1.40~1.80(6H, m), 2.90(6H, m),<br>3.40~4.00(6H, m), 4.34(2H, q, J=7), 4.50(1H, m), 7.17(4H, s),<br>8.03(1H, brt), 8.51(1H, s). |
| 52 | oil | 1.26(3H, t, J=7),1.37(3H, t, J=7), 1.40~1.80(6H, m), 2.90(4H, m),<br>3.50~4.20(8H, m), 4.34(2H, q, J=7), 4.70(1H, m), 6.87(2H, d J=9), |

TABLE 48-continued

| No | mp | $^1$H-NMR (CDCl$_3$) δ ppm |
|---|---|---|
| 53 | 43.5~44° C. | 7.14(2H, d, J=9), 8.02(1H, brt), 8.51(1H, s).<br>0.92(3H, t, J=7), 1.19(3H, t, J=7), 1.25(3H, t, J=7), 1.41(3H, t, J=7),<br>1.88(2H, m), 2.89(2H, t, J=7), 2.92(2H, q, J=7), 3.51(2H, q, J=7),<br>3.61(2H, t, J=7), 4.39(2H, q, J=7), 5.20(1H, q, J=7), 7.18(2H, d, J=8),<br>7.25(2H, d, J=8), 8.47(1H, s), 8.51(1H, d, J=7). |
| 54 | oil | 1.26(3H, t, J=7), 1.37(3H, t, J=7), 2.43(3H, s), 2.80~2.96(8H, m),<br>3.74(2H, t, J=7), 4.34(2H, q, J=7), 7.16(4H, s), 8.02(1H, brt),<br>8.52(1H, s). |

TABLE 49

| No | mp | 1H-NMR (CDCl3) δ ppm |
|---|---|---|
| 55 | oil | 1.10(3H, t, J=7), 1.26(3H, t, J=7), 1.37(3H, t, J=7), 2.67(2H, q, J=7),<br>2.87(8H, m), 3.74(2H, t, J=7), 4.34(2Ha, q, J=7), 7.16(4H, s),<br>8.02(1H, brt), 8.51(1H, s). |
| 56 | oil | 1.26(3H, t, J=7), 1.36(3H, t, J=7), 2.31(6H, s), 2.54(2H, m),<br>2.78(2H, m), 2.89(2H, t, J=7), 2.92(2H, q, J=7), 3.74(2H, t, J=7),<br>4.34(2H, q, J=7), 7.15(4H, s), 8.02(1H, brt), 8.52(1H, s). |
| 57 | 32~33° C. | 1.09(6H, t, J=7), 1.26(3H, t, J=7), 1.36(3H, t, J=7), 2.65(4H, q, J=7),<br>2.74(4H, m), 2.90(2H, t, J=7), 2.91(2H, q, J=7), 3.74(2H, t, J=7),<br>4.34(2H, q, J=7), 7.15(4H, s), 8.02(1H, brt), 8.52(1H, s). |
| 58 | oil | 0.97(3H, t, J=7), 1.20(3H, t, J=7), 1.26(3H, t, J=7), 1.44(2H, m),<br>1.74(2H, m), 2.88(4H, t, J=7), 2.93(2H, q, J=7), 3.51(2H, q, J=7),<br>3.61(2H, t, J=7), 3.74(2H, q, J=7), 4.28(2H, q, J=7), 7.16(4H, s),<br>8.04(1H, brt), 8.52(1H, s). |
| 59 | oil | 1.15(3H, t, J=7), 1.20(3H, t, J=7), 2.86(4H, t, J=7), 2.87(2H, q, J=7),<br>3.50(2H, q, J=7), 3.61(2H, t, J=7), 3.72(2H, q, J=7), 5.30(2H, s),<br>7.15(4H, s), 7.38(5H, s), 8.00(1H, brt), 8.52(1H, s). |

TABLE 50

| No | mp | 1H-NMR (CDCl3) δ ppm |
|---|---|---|
| 60 | oil | 1.25(3H, t, J=7), 1.26(3H, t, J=7), 1.37(3H, t, J=7), 2.57(2H, q, J=7),<br>2.70~3.00(8H, m), 3.74(2H, q, J=7), 4.34(2H, q, J=7), 7.16(4H, s),<br>8.02(1H, brt), 8.52(1H, s). |
| 61 | 44~44.5° C. | 1.26(3H, t, J=7), 1.32(6H, d, J=6), 1.36(3H, t, J=7), 2.85(2H, t, J=7),<br>2.92(2H, q, J=7), 3.73(2H, q, J=7), 4.36(2H, q, J=7), 4.50(1H, m),<br>6.83(2H, d, J=9), 7.13(2H, d, J=9), 8.02(1H, brt), 8.52(1H, s). |
| 62 | oil | 1.01(6H, d, J=7), 1.26(3H, t, J=7), 1.37(3H, t, J=7), 2.06(1H, m),<br>2.86(2H, t, J=7), 2.92(2H, q, J=7), 3.69(2H, d, J=7), 3.73(2H, q, J=7),<br>4.34(2H, q, J=7), 6.84(2H, d, J=9), 7.14(2H, d, J=9), 8.02(1H, brt),<br>8.52(1H, s). |
| 63 | oil | 0.97(3H, d, J=7), 1.26(3H, t, J=7), 1.28(3H, d, J=6), 1.36(3H, t, J=7),<br>1.70(2H, m), 2.85(2H, t, J=7), 2.91(2H, q, J=7), 3.72(2H, q, J=7),<br>4.23(1H, m), 4.27(2H, q, J=7), 6.84(2H, d, J=9), 7.14(2H, d, J=9),<br>8.01(1H, brt), 8.52(1H, s). |

TABLE 51

| No | mp | $^1$H-NMR (CDCl$_3$) δ ppm |
|---|---|---|
| 64 | oil | 0.95(6H, d, J=7), 1.26(3H, t, J=7), 1.36(3H, t, J=7), 1.66(2H, q, J=7),<br>1.80(1H, m), 2.86(2H, t, J=7), 2.92(2H, q, J=7), 3.72(2H, q, J=7),<br>3.96(2H, t, J=7), 4.34(2H, q, J=7), 6.84(2H, d, J=9), 7.14(2H, d, J=9),<br>8.01(1H, brt), 8.52(1H, s). |
| 65 | oil | 0.94(3H, d, J=7), 1.26(3H, t, J=7), 1.28(3H, d, J=7), 1.36(3H, t, J=7),<br>1.47(2H, m), 1.70(2H, m), 2.85(2H, t, J=7), 2.93(2H, q, J=7),<br>3.72(2H, q, J=7), 4.35(2H, q, J=7), 4.35(1H, m), 6.83(2H, d, J=9),<br>7.14(2H, d, J=9), 8.01(1H, brt), 8.52(1H, s). |
| 66 | oil | 0.93(3H, t, J=7), 1.26(3H, t, J=7), 1.42(3H, t, J=7), 1.88(2H, m),<br>2.94(2H, q, J=7), 4.39(2H, q, J=7), 5.20(1H, q, J=7), 6.80~7.05(6H, m), |

TABLE 51-continued

| No | mp | ¹H-NMR (CDCl₃) δ ppm |
|---|---|---|
| | | 7.29(2H, s), 8.40(1H, s), 8.56(1H, d, J=7). |
| 67 | 52–53° C. | 1.22(3H, t, J=7), 1.35(3H, t, J=7), 2.54(3H, s), 2.86(2H, t, J=7), 2.89(2H, q, J=7), 3.74(2H, q, J=7), 3.87(3H, s), 3.88(3H, s), 4.30(2H, q, J=7), 6.74(1H, s), 6.77(2H, m), 8.37(1H, brt). |
| 68 | oil | 1.26(3H, t, J=7), 1.34(3H, t, J=7), 2.87(2H, t, J=7), 2.90(2H, q, J=7), 3.74(2H, q, J=7), 3.86(3H, s), 3.88(3H, s), 4.33(2H, q, J=7), 6.75(3H, m), 8.06(1H, brt), 8.52(1H, s). |

TABLE 52

| No | mp | ¹H-NMR (CDCl3) δ ppm |
|---|---|---|
| 69 | 99–100° C. | 1.32(3H, t, J=7), 1.38(3H, t, J=7), 2.91(2H, t, J=7), 3.04(2H, q, J=7), 3.86(2H, q, J=7), 3.86(3H, s), 3.88(3H, s), 4.34(2H, q, J=7), 6.84(3H, m), 7.46(5H, m), 8.02(1H, brt). |
| 70 | 91–92° C. | 1.26(3H, t, J=7), 1.37(3H, t, J=7), 2.87(2H, t, J=7), 2.92(2H, q, J=7), 3.74(2H, q, J=7), 3.95(2H, t, J=5), 4.04(2H, t, J=5), 4.37(2H, q, J=7), 6.86(2H, d, J=9), 7.15(2H, d, J=9), 8.04(1H, brt), 8.52(1H, s). |
| 71 | 44–45.5° C. | 1.26(3H, t, J=7), 1.37(3H, t, J=7), 2.87(2H, t, J=7), 2.92(2H, q, J=7), 3.09(3H, s), 3.72(2H, q, J=7), 4.22(2H, t, J=5), 4.34(2H, q, J=7), 4.56(2H, t, J=5), 6.84(2H, d, J=9), 7.16(2H, d, J=9), 8.02(1H, brt), 8.52(1H, s). |
| 72 | 37–41° C. | 1.26(3H, t, J=7), 1.37(3H, t, J=7), 2.18(3H, s), 2.73(2H, m), 2.90(6H, m), 3.74(2H, q, J=7), 4.34(2H, q, J=7), 7.16(4H, s), 8.03(1H, brt), 8.51(1H, s). |

TABLE 53

| No | mp | ¹H-NMR (CDCl₃) δ ppm |
|---|---|---|
| 73 | 76–78° C. | 1.26(3H, t, J=7), 1.38(3H, t, J=7), 2.58(3H, s), 2.97(6H, m), 3.07(2H, m), 3.74(2H, q, J=7), 4.34(2H, q, J=7), 7.16(4H, s), 8.07(1H, brt), 8.51(1H, s). |
| 74 | 208–211° C. | 0.95(3H, t, J=7), 1.39(3H, t, J=7), 1.41(2H, m), 1.73(2H, m), 2.91(2H, t, J=7), 3.36(2H, q, J=7), 3.82(2H, q, J=7), 3.93(2H, t, J=7), 6.48(2H, d, J=9), 7.16(2H, d, J=9), 8.70(1H, s), 11.01(1H, brs). |
| 75 | 214–216° C. | 1.29(9H, s), 1.39(3H, t, J=7), 2.92(2H, q, J=7), 3.34(2H, q, J=7), 3.85(2H, q, J=7), 7.17(2H, d, J=8), 7.33(2H, d, J=8), 8.53(1H, s), 10.68(1H, brs). |
| 76 | 51.5–52.5° C. | 1.27(3H, t, J=7), 1.38(3H, t, J=7), 2.92(2H, t, J=7), 2.93(2H, q, J=7), 3.75(2H, q, J=7), 4.35(2H, q, J=7), 6.48(1H, d, J=74), 7.06(2H, d, J=8), 7.23(2H, d, J=8), 8.06(1H, brt), 8.52(1H, s). |
| 77 | 66–68° C. | 1.26(3H, t, J=7), 1.38(3H, t, J=7), 2.27(3H, s), 2.28(3H, s), 2.86(2H, t, J=7), 2.94(2H, q, J=7), 3.69(2H, q, J=7), 4.34(2H, q, J=7), 7.04(3H, s), 8.01(1H, brt), 8.51(1H, s). |

TABLE 54

| No | mp | ¹H-NMR (CDCl₃) δ ppm |
|---|---|---|
| 87 | 49–51° C. | 1.37(3H, t, J=7), 1.40(3H, t, J=7), 2.62(3H, s), 2.86(2H, t, J=7), 3.73(2H, q, J=7), 4.01(2H, q, J=7), 4.34(2H, q, J=7), 6.84(2H, d, J=9), 7.14(2H, d, J=9), 8.23(1H, brt), 8.47(1H, s). |
| 88 | 72–73° C. | 1.25(3H, t, J=7), 1.41(3H, t, J=7), 2.86(2H, t, J=7), 2.91(2H, q, J=7), 3.72(2H, q, J=7), 3.87(3H, s), 4.01(2H, q, J=7), 6.84(2H, d, J=9), 7.15(2H, d, J=9), 7.97(1H, brt), 8.52(1H, s). |
| 91 | 41.5–45.5° C. | 1.36(3H, t, J=7), 1.40(3H, t, J=7), 2.48(3H, s), 2.58(3H, s), 2.84(2H, t, J=7), 3.74(2H, q, J=7), 4.01(2H, q, J=7), 4.31(2H, q, J=7), 6.84(2H, d, J=8), 7.14(2H, d, J=8), 8.22(1H, brt). |
| 93 | 34–36° C. | 1.03(3H, t, J=7), 1.37(3H, t, J=7), 1.80(2H, m), 2.62(3H, s), 2.86(2H, t, J=7), 3.73(2H, q, J=7), 3.90(2H, t, J=7), 4.34(2H, q, J=7), 6.84(2H, d, J=9), 7.14(2H, d, J=9), 8.22(1H, brt), 8.47(1H, s). |
| 98 | 48–49° C. | 1.03(3H, t, J=7), 1.36(3H, t, J=7), 1.80(2H, m), 2.48(3H, s), |

TABLE 54-continued

| No | mp | $^1$H-NMR (CDCl$_3$) δ ppm |
|---|---|---|
| 100 | oil | 2.59(3H, s), 2.85(2H, t, J=7), 3.72(2H, q, J=7), 3.90(2H, t, J=7), 4.32(2H, q, J=7), 6.84(2H, d, J=8), 7.13(2H, d, J=8), 8.14(1H, brt).<br>1.32(6H, d, J=7), 1.37(3H, t, J=7), 2.62(3H, s), 2.86(2H, t, J=7), 3.73(2H, q, J=7), 4.34(2H, q, J=7), 4.51(1H, m), 6.83(2H, d, J=9), 7.13(2H, d, J=9), 8.23(1H, brt), 8.47(1H, s). |

TABLE 55

| No | mp | $^1$H-NMR (CDCl$_3$) δ ppm |
|---|---|---|
| 102 | 36~38° C. | 1.25(3H, t, J=7), 1.32(6H, d, J=7), 2.86(2H, t, J=7), 2.91(2H, q, J=7), 3.72(2H, q, J=7), 3.86(3H, s), 4.52(1H, m), 6.84(2H, d, J=9), 7.14(2H, d, J=9), 7.96(1H, brt), 8.52(1H, s). |
| 105 | 42.5~48.5° C. | 1.32(6H, d, J=6), 1.36(3H, t, J=7), 2.48(3H, s), 2.58(3H, s), 2.84(2H, t, J=7), 3.72(2H, q, J=7), 4.31(2H, q, J=7), 4.51(1H, m), 6.83(2H, d, J=8), 7.14(2H, d, J=8), 8.21(1H, brt). |
| 107 | oil | 0.97(3H, t, J=7), 1.49(2H, q, J=7), 1.76(2H, t, J=7), 2.60(3H, s), 2.86(2H, t, J=7), 3.73(2H, q, J=7), 3.86(3H, s), 3.94(2H, t, J=7), 6.84(2H, d, J=9), 7.14(2H, d, J=9), 8.18(1H, brt), 8.48(1H, s). |
| 109 | 62~63° C. | 0.97(3H, t, J=7), 1.36(3H, t, J=7), 1.48(2H, m), 1.73(2H, m), 2.48(3H, s), 2.58(3H, s), 2.84(2H, t, J=7), 3.73(2H, q, J=7), 3.94(H, t, J=7), 4.31(2H, q, J=7), 6.83(2H, d, J=8), 7.14(2H, d, J=8), 8.20(1H, brt). |
| 111 | 45.5~46.5° C. | 1.02(6H, d, J=7), 1.25(3H, t, J=7), 2.07(1H, m), 2.86(2H, t, J=7), 2.91(2H, q, J=7), 3.70(2H, d, J=7), 3.72(2H, q, J=7), 3.87(3H, s), 6.85(2H, d, J=9), 7.14(2H, d, J=9), 7.97(1H, brt), 8.53(1H, s). |

TABLE 56

| No | mp | $^1$H-NMR (CDCl$_3$) δ ppm |
|---|---|---|
| 113 | 42~45° C. | 1.01(6H, d, J=7), 1.37(3H, t, J=7), 2.07(1H, m), 2.62(3H, s), 2.88(2H, t, J=7), 3.70(2H, d, J=7), 3.72(2H, q, J=7), 4.34(2H, q, J=7), 6.84(2H, d, J=9), 7.14(2H, d, J=9), 8.23(1H, brt), 8.48(1H, s). |
| 114 | 58~61° C. | 1.01(6H, d, J=6), 1.36(3H, t, J=7), 2.08(1H, m), 2.48(3H, s), 2.59(3H, s), 2.85(2H, t, J=7), 3.70(2H, d, J=6), 3.71(2H, q, J=7), 4.32(2H, q, J=7), 6.83(2H, d, J=8), 7.14(2H, d, J=8), 8.21(1H, brt). |
| 118 | 51~52° C. | 1.26(3H, t, J=7), 2.92(2H, q, J=7), 2.93(2H, t, J=7), 3.75(2H, q, J=7), 3.88(3H, s), 6.49(1H, t, J=74), 7.07(2H, d, J=9), 7.23(2H, d, J=9), 8.04(1H, brt), 8.53(1H, s). |
| 120 | 50~52° C. | 1.38(3H, t, J=7), 2.63(3H, s), 2.92(2H, t, J=7), 3.75(2H, q, J=7), 4.34(2H, q, J=7), 6.49(1H, t, J=75), 7.06(2H, d, J=9), 7.23(2H, d, J=9), 8.28(1H, brt), 8.48(1H, s). |

TABLE 57

| No | mp | $^1$H-NMR (CDCl$_3$) δ ppm |
|---|---|---|
| 121 | 61~62° C. | 1.36(3H, t, J=7), 2.48(3H, s), 2.58(3H, s), 2.90(2H, t, J=7), 3.74(2H, q, J=7), 4.34(2H, q, J=7), 6.47(1H, t, J=74), 7.05(2H, d, J=8), 7.24(2H, d, J=8), 8.25(1H, brt). |
| 125 | 31~33° C. | 0.92(3H, t, J=7), 1.36(3H, t, J=7), 1.31-1.64(4H, m), 2.58(2H, t, J=7), 2.62(3H, s), 2.89(2H, t, J=7), 3.74(2H, q, J=7), 4.33(2H, q, J=7), 7.13(4H, m), 8.21(1H, brt), 8.48(1H, s). |
| 156 | 48~49° C. | 0.98(3H, t, J=7), 1.37(3H, t, J=7), 1.51(2H, m), 1.77(2H, m), 2.20(3H, s), 2.62(3H, s), 2.83(2H, t, J=7), 3.71(2H, q, J=7), 3.94(2H, t, J=7), 4.33(2H, q, J=7), 6.75(1H, d, J=9), 7.00(1H, d, J=9), 7.01(1H, s), 8.21(1H, brt), 8.48(1H, s). |
| 163 | 50~51° C. | 0.98(3H, t, J=7), 1.38(3H, t, J=7), 1.52(2H, m), 1.81(2H, m), 2.63(3H, s), 2.84(2H, t, J=7), 3.72(2H, q, J=7), 4.01(2H, t, J=7), 4.35(2H, q, J=7), 6.85(1H, d, J=9), 7.05(1H, dd, J=9,2), 7.23(1H, d, J=2), 8.25(1H, brt), 8.48(1H, s). |
| 164 | 65.5~66.5° C. | 0.98(3H, t, J=7), 1.36(3H, t, J=7), 1.52(2H, m), 1.79(2H, m), |

TABLE 57-continued

| No | mp | ¹H-NMR (CDCl₃) δ ppm |
|---|---|---|
| | | 2.49(3H, s), 2.59(3H, s), 2.82(2H, t, J=7), 3.72(2H, q, J=7), 4.07(2H, t, J=7), 4.33(2H, q, J=7), 6.85(1H, d, J=8), 7.05(1H, dd, J=8,2), 7.23(1H, d, J=2), 8.24(1H, brt). |

TABLE 58

| No | mp | ¹H-NMR (CDCl₃) δ ppm |
|---|---|---|
| 176 | oil | 1.26(3H, t, J=7), 1.37(3H, t, J=7), 2.86(2H, t, J=7), 2.92(2H, q, J=7), 3.72(2H, q, J=7), 4.34(2H, q, J=7), 4.51(2H, d, J=5), 5.28(1H, d, J=10), 5.40(1H, d, J=17), 6.04(1H, m), 6.86(2H, d, J=9), 7.15(2H, d, J=9), 8.02(1H, brt), 8.52(1H, s). |
| 177 | 47–48.5° C. | 1.26(3H, t, J=7), 1.37(3H, t, J=7), 2.51(1H, t, J=2), 2.88(2H, t, J=7), 2.92(2H, q, J=7), 3.72(2H, q, J=7), 4.34(2H, q, J=7), 4.68(2H, d, J=2), 6.93(2H, d, J=9), 7.17(2H, d, J=9), 8.02(1H, brt), 8.52(1H, s). |
| 184 | oil | 0.97(3H, t, J=7), 1.25(3H, t, J=7), 1.49(2H, m), 1.76(2H, m), 2.86(2H, t, J=7), 2.93(2H, q, J=7), 3.72(2H, q, J=7), 3.94(2H, t, J=7), 4.77(2H, d, J=6), 5.31(1H, d, J=11), 5.38(1H, d, J=19), 5.98(1H, m), 6.84(2H, d, J=9), 7.13(2H, d, J=9), 8.00(1H, brt), 8.53(1H, s). |
| 185 | 59–60.5° C. | 0.97(3H, t, J=7), 1.28(3H, t, J=7), 1.48(2H, m), 1.76(2H, m), 2.54(1H, t, J=2), 2.86(2H, t, J=7), 2.97(2H, q, J=7), 3.73(2H, q, J=7), 3.94(2H, t, J=7), 4.88(2H, d, J=2), 6.84(2H, d, J=9), 7.13(2H, d, J=9), 8.01(1H, brt), 8.54(1H, s). |

TABLE 59

| No | mp | ¹H-NMR (CDCl₃) δ ppm |
|---|---|---|
| 324 | oil | 1.26(3H, t, J=7), 1.42(3H, t, J=7), 1.56(3H, d, J=7), 2.94(2H, q, J=7), 4.39(2H, q, J=7), 5.41(1H, quintet, J=7), 6.48(1H, t, J=75), 7.08(2H, d, J=8), 7.36(2H, d, J=8), 8.46(1H, d, J=7), 8.47(1H, s). |
| 325 | oil | 0.94(3H, t, J=7), 1.26(3H, t, J=7), 1.43(3H, t, J=7), 1.89(2H, m), 2.94(2H, q, J=7), 4.41(2H, q, J=7), 5.20(1H, q, J=7), 6.48(1H, t, J=74Hz), 7.07(2H, d, J=8), 7.32(2H, d, J=8), 8.44(1H, s), 8.57(1H, d, J=7). |
| 326 | 46.5–47.5° C. | 1.24(3H, t, J=7), 1.37(3H, t, J=7), 2.62(3H, s), 2.86(2H, t, J=7), 3.60(2H, q, J=7), 3.72(2H, q, J=7), 3.78(2H, t, J=5), 4.10(2H, t, J=5), 4.33(2H, q, J=7), 6.87(2H, d, J=8), 7.14(2H, d, J=8), 8.23(1H, brt), 8.47(1H, s). |
| 327 | 53.5–54.5° C. | 1.24(3H, t, J=7), 1.36(3H, t, J=7), 2.49(3H, s), 2.59(3H, s), 2.85(3H, t, J=7), 3.60(2H, q, J=7), 3.72(2H,q, J=7), 3.79(2H, t, J=5), 4.11(2H, t, J=5), 4.31(2H, q, J=7), 6.87(2H, d, J=8), 7.14(2H, d, J=8), 8.23(1H, brt). |

REFERENCE EXAMPLE 1

Synthesis of 4-(2-(Tetrahydropyran-2-yloxy)ethyl)bromobenzene p-Toluenesulfonic acid (0.30 g) was added to a solution of 4-bromophenethyl alcohol (9.50 g, 47.24 mmol) in methylene chloride (50 ml), and the mixture was stirred under ice-cooling. To the mixture was added 3,4-dihydropyran (5.53 g, 65.74 mmol). After stirring under ice-cooling for 20 minutes, a saturated aqueous solution of sodium bicarbonate (40 ml) was added to the reaction mixture. The resulting mixture was extracted with methylene chloride and dried over magnesium sulfate. After evaporation of the solvent, the desired 4-(2-(tetrahydropyran-2-yloxy)ethyl)bromobenzene was obtained (13.40 g, 99%).

NMR (δ ppm, TMS/CDCl₃): 1.52–1.80 (6H, m), 2.85 (2H, t, J=7 ), 3.43–3.96 (4H,m), 4.57 (1H,t,J=4), 7.12 (2H,d, J=8), 7.39 (2H,d,J=8).

REFERENCE EXAMPLE 2

Synthesis of 4-(2-(Tetrahydropyran-2-yloxy)ethyl)phenethyl Alcohol

Magnesium (1.31 g, 53.90 mmol) was added to a solution of 4-(2-(tetrahydropyran-2-yloxy)ethyl)bromobenzene (14.00 g, 49.09 mmol) in tetrahydrofuran (20 ml). Then dibromoethane (0.1 ml) was added under an atmosphere of nitrogen gas, and the mixture was stirred under room temperature for 1 hour. After cooling to ice-cooling temperature, 2M-ethylene oxide/tetrahydrofuran solution (49.09 ml, 98.18 mmol) was added, and the mixture was stirred at room temperature for 2 hours. Then, water (40 ml) was added to the reaction mixture. The mixture was extracted with ethyl ether and dried over magnesium sulfate. After evaporation of the solvent, the residue was purified by column chromatography on silica gel eluting with n-hexane/ethyl acetate (=8/2)

to give the desired 4-(2-(tetrahydropyran-2-yloxy)ethyl)phenethyl alcohol (6.00 g, 42%).

NMR (δ ppm, TMS/CDCl$_3$): 1.40–1.78 (6H,m), 2.85 (2H,t,J=7), 2.89 (2H,t,J=7), 3.48–3.98 (6H, m), 4.57 (1H,t, J=4), 7.14 (2H,d,J=8), 7.20 (2H,d,J=8).

REFERENCE EXAMPLE 3

Synthesis of
4-(2-(Tetrahydropyran-2-yloxy)ethyl)phenethyl Methanesulfonate

Triethylamine (3.22 g, 31.82 mmol) was added to a solution of 4-(2-(tetrahydropyran-2-yloxy)ethyl)phenethyl alcohol (4.00 g, 15.97 mmol) in methylene chloride (40 ml). The mixture was stirred under ice-cooling, and methanesulfonyl chloride (2.19 g, 19.11 mmol) was added dropwise to the mixture. After the addition, the resulting mixture was stirred under ice-cooling for 10 minutes. Then, water (40 ml) was added. The mixture was extracted with methylene chloride and dried over magnesium sulfate. Evaporation of the solvent gave the desired 4-(2-(tetrahydropyran-2-yloxy)ethyl)phenethyl methanesulfonate (5.24 g, 99%).

NMR (δ ppm, TMS/CDCl$_3$): 1.40–1.78 (6H,m), 2.84 (3H,s), 2.85 (2H,t,J=7), 3.02 (2H,t,J=7), 3.47–3.97 (4H,m), 4.38 (2H,t,J=7), 4.58 (1H,t,J=4), 7.15 (2H,d,J=9), 7.20 (2H, d,J=9).

REFERENCE EXAMPLE 4

Synthesis of
4-(2-(Tetrahydropyran-2-yloxy)ethyl)-1-(2-azidoethyl)benzene

Sodium azide (1.73 g, 26.61 mmol) was added to a solution of 4-(2-(tetrahydropyran-2-yloxy)ethyl)phenethyl methanesulfonate (5.24 g, 15.95 mmol) in N,N-dimethylformamide (50 ml). The mixture was stirred at 100° C. for 1 hour. Water (40 ml) was added to the reaction mixture. The mixture was extracted with ethyl ether and dried over magnesium sulfate. After evaporation of the solvent, the residue was purified by column chromatography on silica gel eluting with n-hexane/ethyl acetate (=20/1) to give the desired 4-(2-(tetrahydropyran- 2-yloxy)ethyl)-1-(2-azidoethyl)benzene (4.30 g, 98%).

NMR (δ ppm, TMS/CDCl$_3$): 1.53–1.80 (6H,m), 2.86 (2H,t,J=7), 2.88 (2H,t,J=7), 3.48 (2H,t,J=7),3.48–3.90 (4H, m), 4.58 (1H,t,J=4), 7.13 (2H,d,J=8), 7.20 (2H,d,J=8).

REFERENCE EXAMPLE 5

Synthesis of
4-(2-(Tetrahydropyran-2-yloxy)ethyl)phenethylamine

To a solution of 4-(2-(tetrahydropyran-2 -yloxy)ethyl)-1-(2-azidoethyl)benzene (4.30 g, 15.61 mmol) in ethanol was added 10% palladium-carbon (0.10 g). The mixture was stirred under an atmosphere of hydrogen gas at room temperature for 16 hours. Then 10% palladium-carbon was filtered off, and the solvent was evaporated. The residue was purified by column chromatography on silica gel eluting with ethyl acetate/methanol (=8/2) to give the desired 4-(2-(tetrahydropyran-2-yloxy)ethyl)phenethylamine (2.80 g, 72%).

NMR (δ ppm, TMS/CDCl$_3$): 1.53–1.80 (8H, m), 2.73 (2H,t,J=7), 2.89 (2H,t,J=7), 2.95 (2H,t,J=7), 3.47–3.90 (4H,m), 4.58 (1H,t,J=4), 7.11 (2H,d,J=8), 7.18 (2H,d,J=8).

EXAMPLE 19

A mixture of 2 parts of the Compound No. 2 and 98 parts of talc is pulverized to obtain a powder.

EXAMPLE 20

A suspension is prepared by mixing 40 parts of Compound No. 3, 10 parts of sodium lignin sulfonate and 50 parts of water.

EXAMPLE 21

A solution is prepared by mixing 10 parts of Compound No. 8, 1 part of Tween 20 (trade mark) and 89 parts of isopropyl alcohol.

EXAMPLE 22

A wettable powder is prepared by mixing 50 parts of Compound No. 10, 6 parts of sodium alkylbenzenesulfonate, 4 parts of sodium lignin sulfonate and 40 parts of clay and pulverizing the mixture.

EXAMPLE 23

Granules are prepared by mixing 5 parts of Compound No. 12, 90 parts of a mixture of equal amounts of bentonite and talc and 5 parts of sodium alkylbenzene sulfonate, pulverizing the mixture and granulating the pulverized mixture.

EXAMPLE 24

An emulsion is prepared by mixing and dispersing 25 parts of Compound No. 18, 8 parts of polyoxyethylene alkylphenyl ether, 2 parts of sodium alkylbenzene sulfonate and 65 parts of xylene.

EXAMPLE 25

A mixture of 2 parts of The Compound No. 20 and 98 parts of talc is pulverized to obtain a powder.

EXAMPLE 26

A suspension is prepared by mixing 40 parts of Compound No. 20, 10 parts of sodium lignin sulfonate and 50 parts of water.

EXAMPLE 27

A solution is prepared by mixing 10 parts of Compound No. 61, 1 part of Tween 20 (trade mark) and 89 parts of isopropyl alcohol.

EXAMPLE 28

A wettable powder is prepared by mixing 50 parts of Compound No. 61, 6 parts of sodium alkylbenzenesulfonate, 4 parts of sodium lignin sulfonate and 40 parts of clay and pulverizing the mixture.

EXAMPLE 29

Granules are prepared by mixing 5 parts of Compound No. 62, 90 parts of a mixture of equal amounts of bentonite and talc and 5 parts of sodium alkylbenzene sulfonate, pulverizing the mixture and granulating the pulverized mixture.

EXAMPLE 30

An emulsion is prepared by mixing and dispersing 25 Darts of Compound No. 61, 8 parts of polyoxyethylene alkyl phenyl ether, 2 parts of sodium alkyl benzene sulfonate and 65 parts of xylene.

EXAMPLE 31

A mixture of 2 parts of Compound No. 63 and 98 parts of talc is pulverized to obtain a powder.

EXAMPLE 32

A suspension is prepared by mixing 40 parts of Compound No. 63, 10 parts of sodium lignin sulfonate and 50 parts of water.

EXAMPLE 33

A solution is prepared by mixing 10 parts of Compound No. 63, 1 part of Tween 20 (trade mark) and 89 parts of isopropyl alcohol.

EXAMPLE 34

A wettable powder is prepared by mixing 50 parts of Compound No. 64, 6 parts of sodium alkylbenzenesulfonate, 4 parts of sodium lignin sulfonate and 40 parts of clay and pulverizing the mixture.

EXAMPLE 35

Granules are prepared by mixing 5 parts of Compound No. 65, 90 parts of a mixture of equal amounts of bentonite and talc and 5 parts of sodium alkylbenzene sulfonate, pulverizing the mixture and granulating the pulverized mixture.

EXAMPLE 36

An emulsion is prepared by mixing and dispersing 25 parts of Compound No. 65, 8 parts of polyoxyethylene alkylphenyl ether, 2 parts of sodium alkylbenzene sulfonate and 65 parts of xylene.

TEST EXAMPLES

The following pot experiments show controlling effect of the various compounds of the present invention on plant diseases by foliar treatment.

EXPERIMENTAL METHOD

In experiments for determination of preventive effect, a liquid sample to be tested was sprayed to test plants. After 24 hours, pathogens were inoculated. In experiments for determination of therapeutic effect, the test plants were inoculated with each pathogen. After 48 hours, a liquid sample to be tested was sprayed to the test plants. The liquid sample was prepared by dissolving the test compound in a small amount of N,N-dimethylformamide and diluting the solution with distilled water containing a spreader to a given concentration. As a control, 4-(2-(4-tert-butylphenyl)ethyl)amino- 5-chloro-6-ethylpyrimidine (Control 1) and 5-chloro-6-ethyl-4-:(α-ethyl-4-(4-fluorophenoxy)benzyl)aminopyrimidine (Control 2) were used. The percent control was calculated according to the following equation and the controlling index was calculated:

Percent control (%) =

$$\frac{\text{severity or number of lesions in untreated plot} - \text{severity or number of lesions in treated plot}}{\text{severity or number of lesions in untreated plot}} \times 100$$

| Controlling index | Percent control |
| --- | --- |
| 5 | not less than 99% |
| 4 | 90 to less than 99% |
| 3 | 70 to less than 90% |
| 2 | 50 to less than 70% |
| 1 | 30 to less than 50% |
| 0 | less than 30% |

TEST EXAMPLE 1

Controlling Effect on Cucumber Powdery Mildew (*Sphaerotheca fuliginea*)

Seeds of cucumber (var.: TSUKUBASHIROIBO; 1.3 to 1.8 leaf stage) were sown in plastic cups (each 9 cm in diameter), followed by cultivation for 2 to 3 weeks. A liquid test sample adjusted to 2.0 ppm was sprayed on the surface of their first leaves. The pathogen was inoculated by spraying to the leaves a conidia suspension of *Sphaerotheca fuliginea* which had been cultured on the cucumber leaves. The plants were kept in a greenhouse at 20° C. for 10 days. The infected area on the leaf was observed, and the percent control was calculated. The results are shown in Table 60.

TABLE 60

Controlling effect on cucumber powdery mildew (*Sphaerotheca fuliginea*)

| | Controlling index | |
| --- | --- | --- |
| Compound No. | Preventive effect | Therapeutic effect |
| 1 | 2 | 4 |
| 2 | 5 | 5 |
| 3 | 5 | 5 |
| 8 | 4 | 4 |
| 10 | 4 | 5 |
| 11 | 5 | 3 |
| 13 | 4 | 4 |
| 17 | 4 | 5 |
| 18 | 3 | 5 |
| 20 | 4 | 5 |
| 61 | 4 | 5 |
| 62 | 5 | 5 |
| 63 | 3 | 5 |
| 64 | 3 | 5 |
| 65 | 2 | 5 |
| Control 1 | 3 | 3 |
| Control 2 | 2 | 2 |

TEST EXAMPLE 2

Controlling Effect on Wheat Powdery Mildew (*Erysiphe graminis*)

Seeds of wheat (var.: Norin No. 61; 2.0 to 2.5 leaf stage) were sown in plastic cups (each 9 cm in diameter), followed by cultivation for about 1 0 days in a greenhouse. A liquid test sample (125 or 31.3 pppm) was sprayed well to the seedling. Inoculation was done by dusting conidia of *Erysiphe graminis* which had been cultured on the cucumber leaves, to the leaves. The plants were kept in a greenhouse at 25° C. for additional 7 days. The infected area on the leaves was observed, and the percent control was calculated. The results are shown in Table 61.

TABLE 61

Controlling effect on wheat powdery mildew
(*Erysiphe graminis*)

| | Controlling index Preventive effect | |
|---|---|---|
| Compound No. | 125 ppm | 31.3 ppm |
| 1 | 5 | 2 |
| 2 | 5 | 4 |
| 3 | 5 | 3 |
| 8 | 5 | 3 |
| 10 | 5 | 2 |
| 11 | 4 | 2 |
| 12 | 5 | 3 |
| 13 | 4 | 1 |
| 17 | 5 | 5 |
| 18 | 5 | 5 |
| 19 | 4 | 4 |
| 20 | 5 | 5 |
| 21 | 4 | 2 |
| 61 | 5 | 5 |
| 62 | 5 | 5 |
| 63 | 5 | 3 |
| 64 | 5 | 4 |
| 65 | 5 | 3 |
| Control 1 | 3 | 0 |
| Control 2 | 0 | 0 |

Insecticidal Activity of the Compound of the Invention

The following test examples show experiments for evaluating insecticidal activity of the compound of the invention against three kinds of injurious insects. The test solution was prepared by dissolving the compound to be tested in a small amount of N,N-dimethylformamide and diluting the solution to a given concentration with distilled water containing a surfactant.

TEST EXAMPLE 3

Insecticidal Activity against Green Peach Aphid
(*Myzus persicae*)

A piece of a Chinese cabbage leaf with a diameter of 3 cm was put, with the back up, on a 0.3% agar gel. Apterous adults were inoculated on it, and kept at 25° C. for 1 day. Then born larvae were counted. Then the adults were removed. A given concentration of the test solution was sprayed on the larvae on the piece of the Chinese cabbage leaf. After 48 hours at 25° C., the dead larvae were counted, and the ratio of the dead insects (i.e., larvae) to the above born larvae was calculated to evaluate the effect. The results are shown in Table 62.

TEST EXAMPLE 4

Insecticidal Activity against Green Rice Leafhopper
(*Nephotettix cincticeps*)

Six to seven paddy seedlings were bound into sheaves, and stem part of the bundle was covered with sponge. The seedlings were fixed in a polyethylene cup with a diameter of 6 cm containing a small amount of water at the bottom part by the sponge, and covered with a cylinder of stainless steel screen mesh. Then ten female adults were released in the cylinder. A given concentration of the test solution was sprayed thereto. After 48 hours at 25° C., the dead insects were counted, and the ratio of the dead insects to the above ten insects was calculated to evaluate the effect. The results are shown in Table 62.

TEST EXAMPLE 5

Miticidal Activity against Two Spotted Spider Mite (*Tetranychus urticae*)

Ten female adults of *Tetranychus urticae* (sensitive population breeded successively using kidney bean leaves) were inoculated on a leaf of kidney bean seedlings in a cup. The Test solution diluted to a given concentration was sprayed, and the kidney beans were kept in a glasshouse. The compounds which prevented damage by the mites after 12 days were evaluated as having the activity.

The results are shown in Table 62 in terms of the percent control at 63 ppm.

TABLE 62

| | Ratio of dead insects at 63 ppm | | Percent control at 63 ppm |
|---|---|---|---|
| Compound No. | *Myzus persicae* | *Nephotettix cincticeps* | *Tetranychus urticae* |
| 1 | 100 | 50 | 100 |
| 2 | 100 | 100 | 100 |
| 3 | 100 | 100 | 100 |
| 10 | 100 | | |
| 11 | 100 | 77 | 100 |
| 14 | 100 | | |
| 18 | 100 | | |
| 19 | 100 | | |
| 20 | 100 | | |
| 61 | 100 | | |
| 62 | 100 | | |
| 63 | 100 | | |
| 64 | 100 | | 100 |
| 65 | 100 | | 100 |

What is claimed is:
1. A compound of the formula (II):

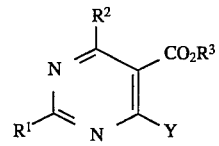

(II)

wherein

Y is a halogen atom;

$R^1$ is (1) a hydrogen atom, (2) $C_{1-6}$ alkyl, (3) $C_{1-6}$ alkylthio, or (4) a heterocyclic group selected from the group consisting of pyridyl, pyrimidinyl, pyrazinyl, thiazolyl, benzothiazolyl, benzofuranyl, benzothienyl, oxazolyl, benzoxazolyl, isoxazolyl, pyrazolyl, imidazolyl and quinolyl, which is unsubstituted or substituted by a halogen atom, $C_{1-4}$ alkyl, halo-$C_{1-4}$ alkyl, or $C_{1-4}$ alkoxy;

$R^2$ is $C_{1-6}$ alkyl; and $R^3$ is (1) a hydrogen atom, (2) $C_{1-6}$ alkyl, (3) $C_{2-6}$ alkenyl, (4) $C_{2-6}$ alkynyl or (5) $C_{6-10}$ aryl-$C_{1-4}$ alkyl.

2. A compound of the formula (IV):

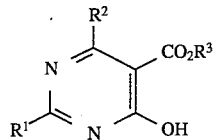
(IV)

wherein $R^1$ is (1) a hydrogen atom, (2) a halogen atom, (3) $C_{1-6}$ alkyl, (4) $C_{1-6}$ alkylthio, (5) a heterocyclic group selected from the group consisting of pyridyl, pyrimidinyl, pyrazinyl, thiazolyl, benzothiazolyl, benzofuranyl, benzothienyl, oxazolyl, benzoxazolyl, isoxazolyl, pyrazolyl, imidazolyl and quinolyl, which is unsubstituted or substituted by a halogen atom, $C_{1-4}$ alkyl, halo-$C_{1-4}$ alkyl, or $C_{1-4}$ alkoxy, (6) phenyl which is unsubstituted or substituted by a halogen atom, $C_{1-4}$ alkyl, halo-$C_{1-4}$ alkyl or $C_{1-4}$ alkoxy;

$R^2$ is $C_{1-6}$ alkyl; and $R^3$ is (1) a hydrogen atom, (2) $C_{1-6}$ alkyl, (3) $C_{2-6}$ alkenyl, (4) $C_{2-6}$ alkynyl or (5) $C_{6-10}$ aryl-$C_{1-4}$ alkyl.

3. A process for producing a compound of the formula (I):

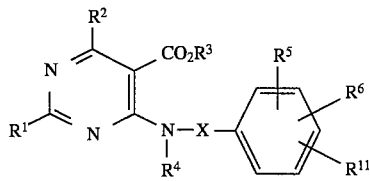
(I)

wherein $R^1$ is a hydrogen atom, halogen atom, alkyl, alkylthio, optionally substituted phenyl or optionally substituted heterocyclic group; $R^2$ is alkyl; $R^3$ is a hydrogen atom, alkyl, alkenyl, alkynyl or aralkyl; $R^4$ is a hydrogen atom or alkyl; $R^5$, $R^6$ and $R^{11}$ each is a hydrogen atom, halogen atom, alkoxy, optionally substituted alkyl, alkenyl, alkynyl, optionally substituted hydroxyl, mono- or dialkylamino, alkylthio, alkylsulfinyl, alkylsulfonyl or nitro; and X is alkylene or alkyleneoxy; or a salt thereof, which process comprises reacting a compound of the formula (V):

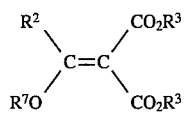
(V)

wherein $R^7$ is alkyl, alkylcarbonyl or alkylsulfonyl, and the other symbols are as defined above, with a compound of the formula (VI):

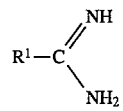
(VI)

wherein $R^1$ is as defined above, or an acid addition salt thereof, to produce a compound of the formula (IV):

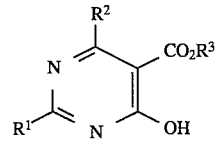
(IV)

wherein each symbol is as defined above; halogenating the compound of the formula (IV) to produce a compound of the formula (II):

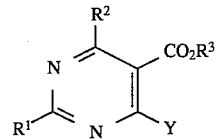
(II)

wherein Y is a halogen atom and the other symbols are as defined above; and reacting the compound of the formula (II) with a compound of the formula (III):

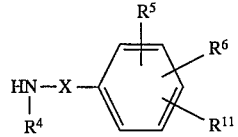
(III)

wherein each symbol is as defined above, to produce the compound of the formula (I).

* * * * *